(12) United States Patent
Goldmakher et al.

(10) Patent No.: US 8,137,669 B2
(45) Date of Patent: Mar. 20, 2012

(54) ELIMINATION OF HETEROGENEOUS OR MIXED CELL POPULATION IN TUMORS

(75) Inventors: Viktor S. Goldmakher, Newton, MA (US); Robert J. Lutz, Wayland, MA (US); Ravi V. J. Chari, Newton, MA (US); Yelena V. Kovtun, Maynard, MA (US); John M. Lambert, Cambridge, MA (US); Rita Steeves, Stoneham, MA (US); Hans K. Erickson, Cambridge, MA (US)

(73) Assignee: Immunogen, Inc., Waltham, MA (US)

( * ) Notice: Subject to any disclaimer, the term of this patent is extended or adjusted under 35 U.S.C. 154(b) by 489 days.

(21) Appl. No.: 12/186,411

(22) Filed: Aug. 5, 2008

(65) Prior Publication Data

US 2009/0076263 A1    Mar. 19, 2009

Related U.S. Application Data

(62) Division of application No. 11/404,001, filed on Apr. 14, 2006, now abandoned.

(60) Provisional application No. 60/671,498, filed on Apr. 15, 2005, provisional application No. 60/781,722, filed on Mar. 14, 2006.

(51) Int. Cl.
*A61K 39/00* (2006.01)

(52) U.S. Cl. .................................... 424/133.1

(58) Field of Classification Search ................ 424/133.1
See application file for complete search history.

(56) References Cited

U.S. PATENT DOCUMENTS

| 5,208,020 A | 5/1993 | Chari et al. |
| 6,441,163 B1 | 8/2002 | Chari et al. |
| 2004/0235840 A1* | 11/2004 | Chari et al. ................ 514/229.5 |

FOREIGN PATENT DOCUMENTS

| WO | 2004/103272 A2 | 12/2004 |
| WO | 2004/110498 A2 | 12/2004 |

OTHER PUBLICATIONS

International Search Report dated Jul. 3, 2008, received in International Application No. PCT/US06/14411.
L.L. Muldoon, et al. "BR98-DOX immunoconjugate target of chemotherapy in brain tumor models" Journal of Neuro-Onology 65; pp. 49-62, 2003, Kluwer Academic Publishers, Netherlands.
R. K. Johnson, et al.; #1926 "Role of a Bystander Effect in the Efficacacy of SB-408075, an Antibody-maytansinoid Complex, in Colon Carcinoma Xenografts", p. 303, Proceedings of the American Association for Cancer Research 91st Annual Meeting, vol. 41, Mar. 2000, San Francisco, CA.
E. A. Neuwelt, M.D. et al: "Effect of Antigenic Heterogeneity on the Efficacy of Enhanced Delivery of Antibody-targeted Chemotherapy in a Human Lung Cancer Intracerebral Xenograft Model in Rats", Neurosurgery, pp. 1406-1413, vol. 53, No. 6, Dec. 2003.
European Search Report dated May 31, 2011, as issued in European Patent Applicaiton No. 06750449.8.

* cited by examiner

*Primary Examiner* — Brandon Fetterolf
*Assistant Examiner* — Christopher R Stone
(74) *Attorney, Agent, or Firm* — Sughrue Mion, PLLC

(57) ABSTRACT

Methods of killing or inhibiting tumors comprising of heterogeneous or mixed cell populations is described. The killing or inhibition of tumors is achieved by selectively targeting a unique ligand suspected of being expressed on a particular cell population to also kill a cell population lacking the unique ligand. These conjugates have therapeutic use as they are delivered to a specific cell population to kill these cells and the cytotoxic drug is released to kill non-targeted cells, thereby eliminating the tumor.

5 Claims, 20 Drawing Sheets

Figs. 4 A, B, C
A
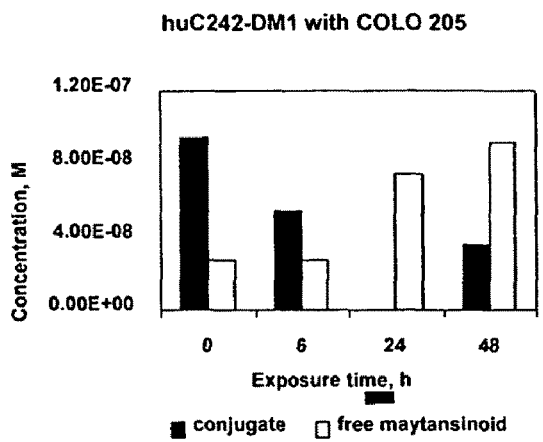
B
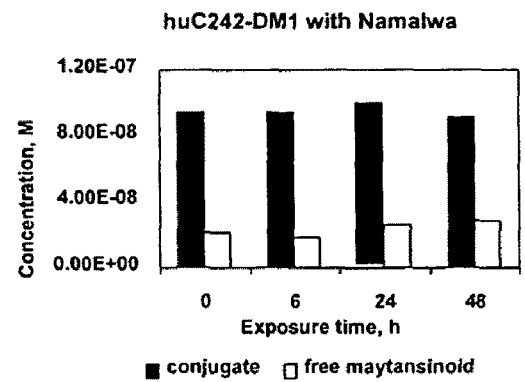
C
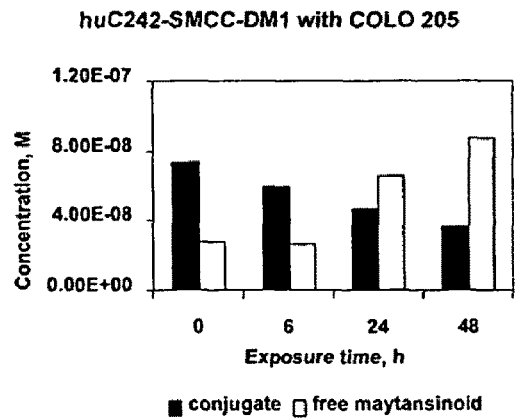

Figure 17 Synthesis of thiomethyl maytansinoids
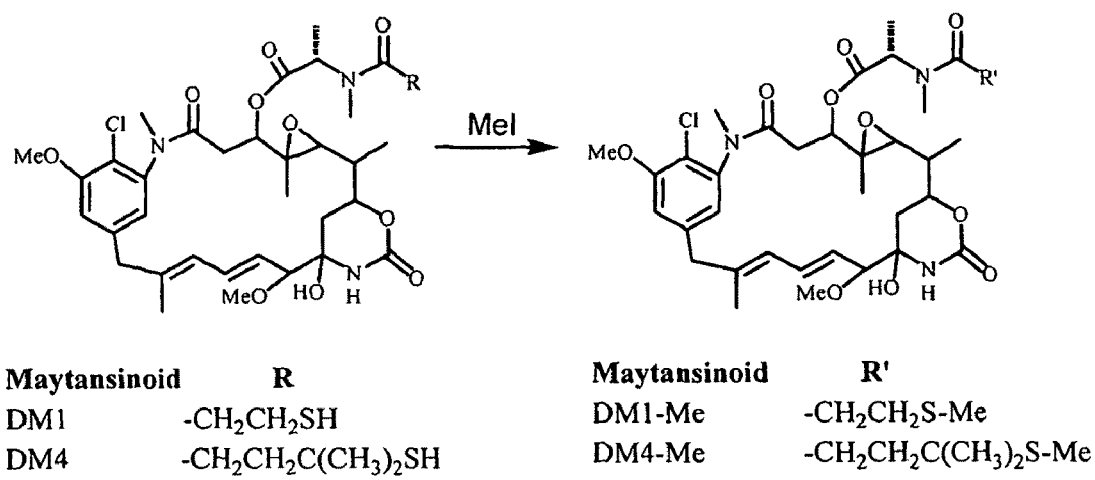
| Maytansinoid | R |
|---|---|
| DM1 | -CH$_2$CH$_2$SH |
| DM4 | -CH$_2$CH$_2$C(CH$_3$)$_2$SH |
| Maytansinoid | R' |
|---|---|
| DM1-Me | -CH$_2$CH$_2$S-Me |
| DM4-Me | -CH$_2$CH$_2$C(CH$_3$)$_2$S-Me |

ELIMINATION OF HETEROGENEOUS OR MIXED CELL POPULATION IN TUMORS

This is a divisional of application Ser. No. 11/404,001 filed Apr. 14, 2006 now abandoned, which claims priority to U.S. provisional application No. 60/671,498, filed Apr. 15, 2005 and to U.S. provisional application No. 60/781,722, filed Mar. 14, 2006. The disclosures of each application is expressly incorporated herein by reference in their entireties.

FIELD OF THE INVENTION

The present invention relates to methods for elimination or killing of heterogeneous or mixed cell populations. In particular, the present invention relates to a method of killing a tumor comprised of heterogeneous or mixed cell populations by selectively targeting a unique ligand, such as an antigen, an epitope or a receptor, that is expressed on a particular cell population to also kill a cell population lacking the unique ligand.

BACKGROUND OF INVENTION

The therapeutic efficacy of cytotoxic anti-cancer drugs can be improved by increasing their selectivity towards cancer cells. One way to achieve this goal is to link a drug covalently to a monoclonal antibody or other type of targeting agent that has selective affinity towards the tumor cells. This approach has been extensively explored with various types of cytotoxic agents, and several types of humanized (or human) antibody-drug conjugates, or immunoconjugates, have been developed that combine high potency and selectivity in killing target tumor cells, long circulation retention times, and lack of immunogenicity. This new generation of highly effective anti-cancer agents includes conjugates of antibodies with maytansinoids, analogues of CC1065, derivatives of taxol (taxoids), of auristatin, and of a calicheamycin γ1. Several maytansinoid (DM1) conjugates are currently in clinical development, and a conjugate of an anti-CD33 antibody with calicheamycin, Mylotarg, has been approved by the Federal Food and Drug Administration for clinical use as an anti-cancer drug.

Many reports have been published detailing attempts to specifically target tumor cells with monoclonal antibody-drug conjugates (Sela et al. in *Immunoconjugates* 189-216 (C. Vogel, ed. 1987); Ghose et al, in *Targeted Drugs* 1-22 (E. Goldberg, ed. 1983); Diener et al, in *Antibody Mediated Delivery Systems* 1-23 (J. Rodwell, ed. 1988); Pietersz et al, in *Antibody Mediated Delivery Systems* 25-53 (J. Rodwell, ed. 1988); Bumol et al, in *Antibody Mediated Delivery Systems* 55-79 (J. Rodwell, ed. 1988). Cytotoxic drugs such as methotrexate, daunorubicin, doxorubicin, vincristine, vinblastine, melphalan, mitomycin C, and chlorambucil have been conjugated to a variety of monoclonal antibodies. In some cases, the drug molecules were linked to the antibody molecules through an intermediary carrier molecule such as serum albumin (Garnett et al. *Cancer Res.* 46:2407-2412 (1986); Ohkawa et al. *Cancer Immumol. Immunother.* 23:81-86 (1986); Endo et al. *Cancer Res.* 47:1076-1080 (1980)), dextran (Hurwitz et al. *Appl. Biochem.* 2:25-35 (1980); Manabi et al. *Biochem. Pharmacol.* 34:289-291 (1985); Dillman et al. *Cancer Res.* 46:4886-4891 (1986); Shoval et al. *Proc. Natl. Acad. Sci.* 85: 8276-8280 (1988)), or polyglutamic acid (Tsukada et al. *J. Natl. Canc. Inst.* 73:721-729 (1984); Kato et al. *J. Med. Chem.* 27:1602-1607 (1984); Tsukada et al. *Br. J. Cancer* 52:111-116 (1985)).

The efficacy of an antibody-drug conjugate is generally compromised by the heterogeneous expression of the target antigen in some tumors, because targeted delivery of conjugated drug via antibody binding to the antigen-positive tumor cells will spare any antigen-negative tumor cells to which the antibody cannot bind. Furthermore, tumor vasculature is an attractive target that is attracting more and more attention as a way to shrink tumors by starving them of their blood supply. Tumor vasculature is usually tumor antigen-negative. It has been reported previously that several classes of antibody-targeted cytotoxic agents are indeed capable of eradicating not only antigen-positive cells but also antigen-negative neighboring cells, a so called "bystander effect". This bystander effect was observed with immunoradionuclides, immunoliposomes, and ADEPT (Allen T M, Nat Rev Cancer 2 (10):750-63 (2002); Muldoon L L, Neurosurgery 53(6): 1406-12 (2003), Muldoon L L and Neuwelt E A, J Neurooncol 65(1):49-62 (2003)). In an abstract published in Proceedings of the American Association for Cancer Research, vol 41, March 2000, the authors describe that a portion of the cleaved DM1 is effluxed by p-glycoprotein and other efflux transporters in a cell. This is because, in the extracellular environment, the free released DM1-thiol readily reacts with cellular molecules having a sulfhydryl group or disulfide bonds, such as in cysteine or cystine, oxidized or reduced glutathione, or proteins (e.g., plasma albumin). Once reacted with these hydrophilic biological molecules, the DM-1 becomes an inactive, mixed disulfide compound, which precludes it from being effective to penetrate neighboring cells and to retain its potency.

Therefore, it would greatly benefit the treatment of various proliferative diseases if cell binding agent-drug conjugates could be designed in such a way so as to provide a more stable and potent form of the free drug to destroy not only the antigen-positive tumor cells, but also any surrounding antigen-negative tumor cells or cells of the neoplastic vasculature, thereby maximizing success in treating tumors by release of stable free drug from the conjugate inside the target cell.

SUMMARY OF THE INVENTION

The objective of the present invention is to provide methods for eliminating heterogeneous or mixed cell populations AB, wherein A represents a cell population selectively expressing a specific ligand and B represents a cell population lacking the ligand expressed by A. The methods generally encompass; delivering a cell-binding agent drug conjugate, linked by a linker comprising a disulfide group, to the selected cell population A that expresses the ligand, allowing the binding of this agent to the ligand in the cell population A, with the option that the drug is internalized into cells comprising the cell population A. A drug attached to cell-binding agent in a conjugate is referred to as a pro-drug; the pro-drug, once cleaved from the conjugate is converted into a cytotoxic drug or "drug" and is capable of undergoing further modification, such as alkylation. A cytotoxic drug or a modified cytotoxic drug is the active pharmaceutical. Thus, in one embodiment, the drug, once cleaved from the conjugate, undergoes alkylation, preferably methylation, which protects the unreacted thiol group from undergoing further modification that would result in inactivation of the drug. The free alkylated drug is effective to kill the cells in the cell population A; and such an "activated" drug is released from the cell population A to induce killing of cells in the cell population B, thereby eliminating the heterogeneous or mixed cell population AB. The term "activated," as used herein, refers to a free drug, preferably a modified free drug, wherein the modification of the free drug enhances its stability or activity. Such modification encompasses alkylation, e.g., methylation, of the drug after it is cleaved from the antibody-drug conjugate.

Thus, it has been unexpectedly found that if a drug undergoes alkylation (e.g., methylation) at the thiol group once the drug is released from the conjugate, the alkylation provides protection to the drug from reacting with cellular molecules having a sulfhydryl group, like cysteine, or proteins (e.g., plasma albumin), which would hinder or inactivate the free drug. As shown in this invention, the alkylated free drug is highly stable, potent, and it readily transfers to and kills antigen negative neighboring cells, thereby killing a heterogeneous or mixed population of cells in a tumor.

Coupled to the above finding is another surprising finding that free drug alkylation is a preferred event if the disulfide bond in the linker, which links the cell-binding agent to the drug, is stabilized by creating a steric hindrance in the vicinity of the disulfide bond. In a preferred embodiment, the disulfide bond is stabilized by providing a steric hindrance on the drug side of the link. The steric hindrance is generally provided by alkyl atoms, such as methyl groups, but other alkyl groups could also be used. The "drug-side," as used herein refers to substitutions on the one $\alpha$-carbon atom of the two $\alpha$-carbon atoms of the disulfide bond that will be connected to the drug after disulfide bond cleavage in the conjugate.

A "heterogeneous or mixed cell population" refers to diversity in a tumor cell population, which includes different phenotypic features or molecular signatures, such as heterogeneity of ligands, e.g., antigens, epitopes or receptors on the surface of tumor cells. It also refers to mixed cell populations in a tumor tissue, such as tumor cells, cells of the tumor vasculature, and cells of the tumor stroma. Furthermore, it also refers to a tumor in which a tumor cell may have undergone spontaneous mutations resulting in a population of genetically heterogeneous cells as it grows from a single malignantly transformed cell. The phenotypic feature could comprise of a tumor cell expressing a ligand, such as an antigen, an epitope or a receptor on the surface of the tumor cell at a particular stage of tumor progression. The same tumor cell may lose the expression of ligands on the surface as the cell undergoes phenotypic change, e.g., by differentiation. The phenotypic change also includes cells losing their ligands by shedding them into the surrounding.

A "heterogeneous or mixed cell population" also refers to virus infected cells, microorganism infected cells, and parasite infected cells, in which a virus, microorganism or a parasite may have undergone spontaneous mutations resulting in a population of genetically or phenotypically heterogeneous cells as it grows from a single cell.

Thus in one aspect, the present invention is a method for targeting a drug to a selected cell population in a tumor wherein at least some of the cells express a particular ligand to kill or eliminate an unrelated cell population within the same tumor which lacks such a ligand. The method comprises contacting a selected cell population or tissue that expresses a particular ligand with a cell-binding agent drug conjugate, wherein one or more drugs is covalently linked to the cell-binding agent via a linker and the selected cell population releases the cytotoxic agent or the "activated" drug to kill or eliminate unrelated cells which lack the ligand expressed by the targeted cell population.

Another aspect of the present invention is a method of eliminating a heterogeneous or mixed cell population by targeting a cell-binding agent drug conjugate to a selected cell population wherein at least some of the cells express a ligand within the heterogeneous or mixed cell population. The ligand is recognized by the cell-binding agent of the conjugate, which has one or more drugs covalently linked via a linker. The cell-binding agent binds to the targeted cells and is internalized, thereby killing the targeted cells. The activated drug is released into the surroundings to induce killing of another selected cell population that lacks the ligand, thereby eliminating the heterogeneous or mixed cell population.

The present invention also teaches a method of killing of cells in a tumor comprising targeting a ligand that was initially expressed on the selected cell population A of a heterogeneous or mixed cell populations AB, and over the course of time shed into the medium. Here, the cell binding agent-drug conjugate is preferably targeted to the shed ligand. The cell binding agent-drug conjugate is cleaved to release the activated drug which diffuses into the neighboring abnormal cells surrounding the shed antigen to induce killing of these cells which comprise a heterogeneous or mixed cell population in a tumor and lack the ligand that was selectively targeted, thereby killing the cells in the tumor.

Figure 1:
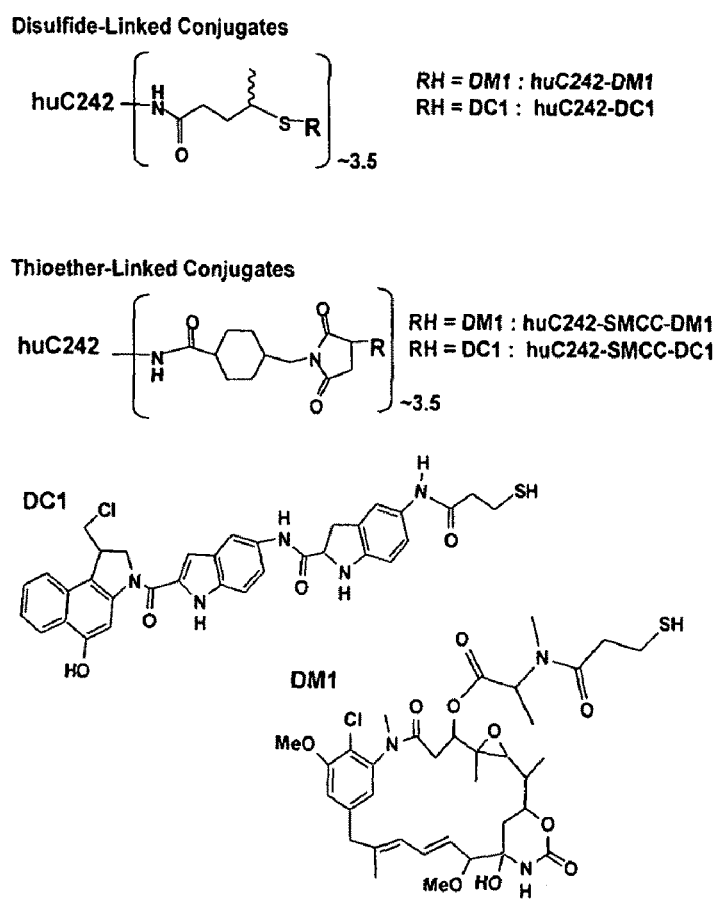
FIG. 1. Structures of antibody-drug conjugates.

A. Effect of COLO 205 cells treated with huC242-DM1, formaldehyde, or UV light, on the proliferation of untreated COLO 205 cells in 3D collagen cell cultures. The untreated cells were mixed with the treated cells at different ratios and the samples were incubated in collagen for 5 days, then viable cells were measured using an MTT assay. The fraction of surviving cells is shown for each cell mixture ratio. Black, grey, and white bars represent the results for cultures with huC242-DM1-treated cells, with formaldehyde-treated cells, and with UV light treated cells, respectively. The experiment was repeated twice with similar results.

B. Effect of COLO 205 cells treated with huC242-DM1 or huC242-SMCC-DM1 on untreated COLO 205, Namalwa, A375, and HepG2 cells when grown in mixed 3D collagen cell cultures. Samples of huC242-DM1 or huC242-SMCC-DM1 treated COLO 205 cells were mixed with equal numbers of Namalwa, A375, HepG2, or untreated COLO 205 cells and the mixed cultures were incubated in a collagen matrix for five days, when the number of viable cells were determined using an MTT assay and compared to those of control samples (untreated cells only). The fraction of surviving cells is shown for each cell line, black bars for COLO 205, gray bars for Namalwa, white bars for A375, and dashed bars for HepG2 cells.

C. Treatment of CanAg-positive COLO 205 cells, CanAg-negative Namalwa cells or mixed COLO 205 and Namalwa cell populations with huC242-DM1, huC242-SMCC-DM1, huC242-DC1, or huC242-SMCC-DC1 in liquid cell culture.

COLO 205 cells, Namalwa cells, and mixed populations of equal numbers of COLO 205 and Namalwa cells were grown in round-bottom wells of tissue culture plates in the absence (left row) or presence (right row) of 1 nM of one of the antibody-drug conjugates. After five days of incubation, photographs of the wells were taken.

D. Results of an experiment analogous to that under C., except that the antigen-positive cell line is SNU-16.

FIG. 4. A cytotoxic maytansinoid gradually accumulates in the supernatant of antigen-positive target cells treated with huC242-DM1.

Samples of CanAg-positive COLO 205 cells (A, C, D, F) and CanAg-negative Namalwa cells (B, E) were incubated with huC242-DM1 (A, B, D, E) or huC242-SMCC-DM1 (C, F). The culture media were withdrawn at the start and after 6, 24, and 48 hours of incubation and assayed for the presence of the conjugate (black bars) and released maytansinoid drug (white bars) (A, B, C), and for cytotoxic activity on CanAg-negative Namalwa cells (D, E, F). Surviving fractions of the cells are plotted vs. concentration of the conjugate in the sample.

FIG. 5. Bystander cytotoxicity of immunoconjugates in xenograft tumor models.

A. Immunohistochemical analysis of mixed COLO 205/Namalwa xenograft tumors grown in SCID mice and treated either with huC242-DM1 or huC242-SMCC-DM1. Slides were stained with murine C242 antibody to detect COLO 205 cells (left column) or an anti-CD38 antibody to detect Namalwa cells (right column). a and b are consecutive sections of an untreated tumor, c and d are from a tumor of the control group of animals treated with PBS, e and f are from a tumor in an animal treated with huC242-SMCC-DM1, and g and h are from a tumor in an animal treated with huC242-DM1. Arrows point to necrotic areas.

B. Activity of huC242-DM1 and huC242-SMCC-DM1 conjugates against xenograft tumors of CanAg-positive target COLO 205 cells (a), antigen-negative Namalwa cells (b), and mixed populations of COLO 205 and Namalwa cells (c). Animals with established tumors of about 100 mm³ size were treated on five consecutive days with PBS (■, control group), huC242-SMCC-DM1 (○, •), or huC242-DM1 (□, ▲) at daily doses of the conjugates that contained 150 µg/kg of linked DM1. Tumor volumes in mm³ were plotted vs. time (days after cell inoculation).

Figure 6:
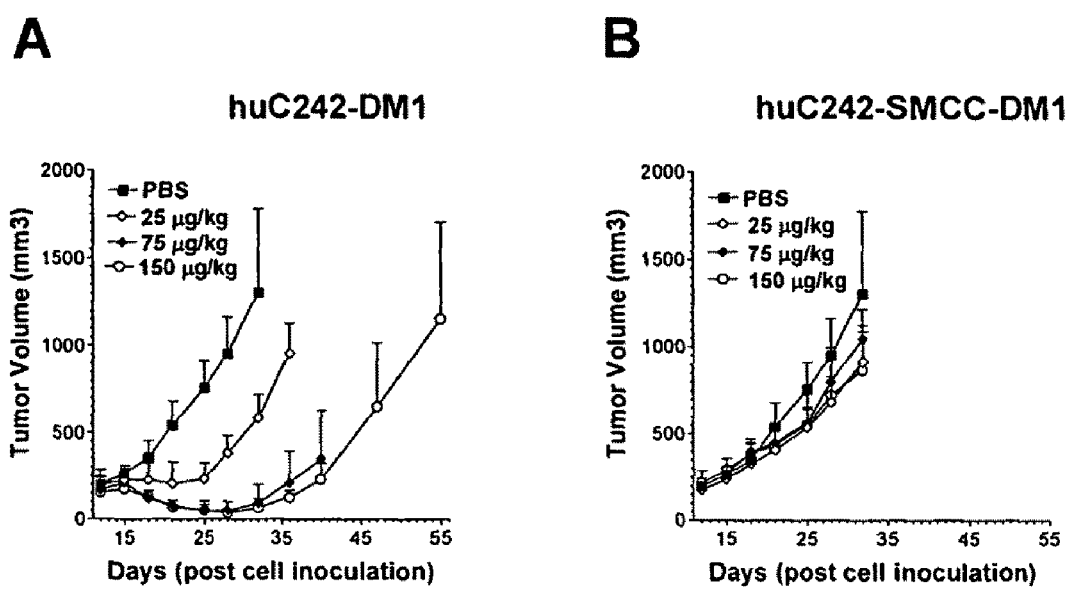

FIG. 6. Activity of huC242-DM1 and huC242-SMCC-DM1 conjugates against HT-29 xenograft tumors, which express the target antigen, CanAg, in a heterogeneous fashion. Groups of five mice bearing 13 day-old subcutaneous tumors of a mean volume of about 170 mm³ were treated on five consecutive days with either PBS (■, control group), huC242-DM1 (A) or with huC242-SMCC-DM1 (B) at daily doses of the conjugates that contained either 25 µg/kg (◇), 75 µg/kg (♦) or 150 µg/kg (○) of linked DM1. Tumor volumes in mm³ were plotted vs. time (days after cell inoculation).

Figure 7:
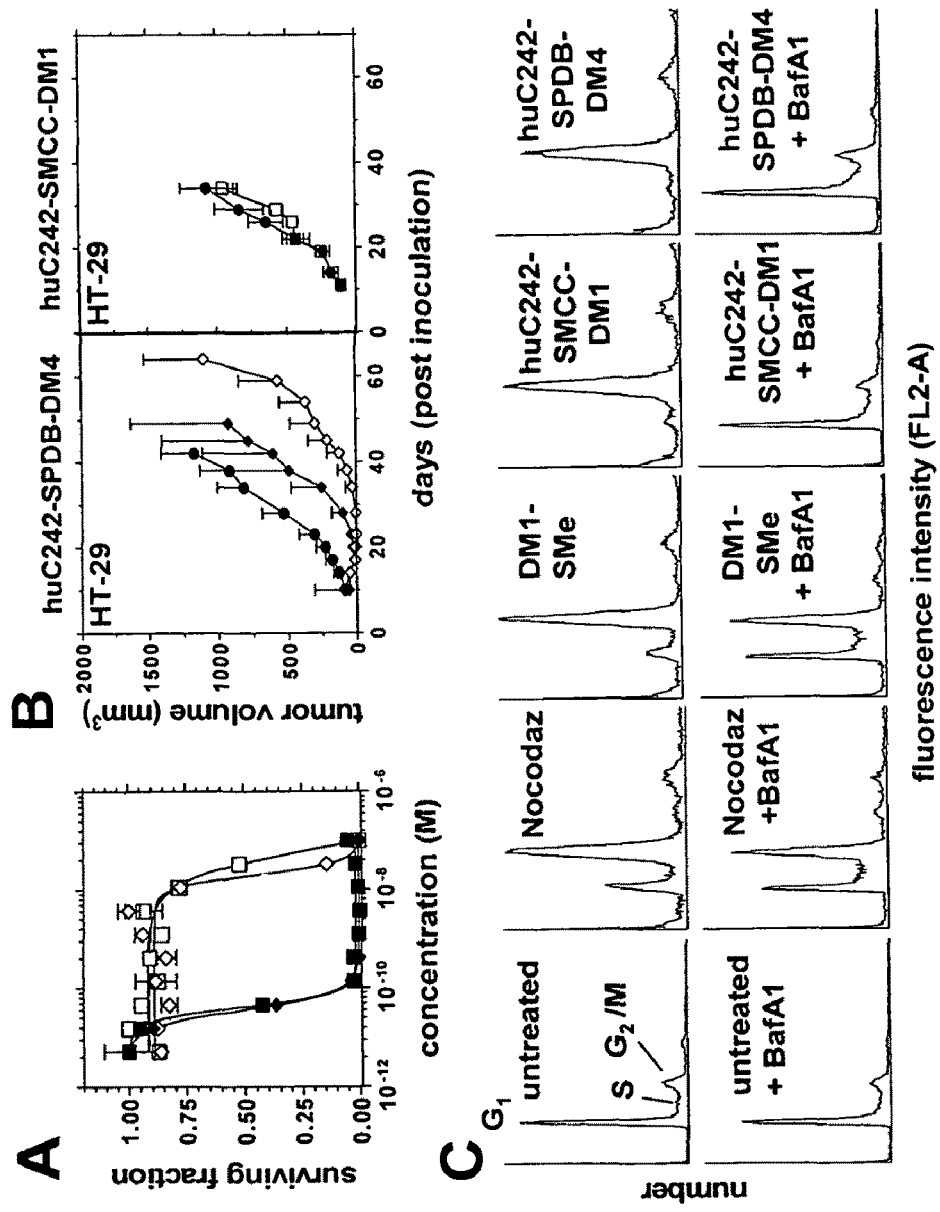

FIG. 7. Cytotoxicity of huC242-SPDB-DM4 and huC242-SMCC-DM1 and their effects on the cell cycle in the presence of the lysosomal inhibitor BafA1. (A) Surviving fractions of antigen-positive COLO 205 (closed symbols) and antigen negative Nalmawa cells (open symbols) were measured using an MTT assay after exposure to different concentrations of huC242-SPDB-DM4 (diamonds) or huC242-SMCC-DM1 (squares) for 4 days, and plotted vs, conjugate concentrations. (B) Antitumor activities of huC242-SPDB-DM4 and huC242-SMCC-DM1 in SCID mice bearing HT-29 human colon tumor xenografts. Doses are based on the amount of conjugated DM4 or DM1. Tumor bearing mice were treated with PBS (closed circles, both panels), a single dose of 50 µg/kg huC242-SPDB-DM4 (open diamonds), 150 µg/kg huC242-SPDB-DM4 (closed diamonds), or five daily injections of huC242-SMCC-DM1 at a dose of 150 µg/kg (open squares). (C) FACS histograms (FL2-A) display DNA contents of asynchronous, exponentially growing COLO 205 cells treated for 20 hours with 0.66 µM nocodazole, $10^{-8}$ M DM1-SMe, $3\times10^{-9}$ M huC242-SMCC-DM1, or $3\times10^{-9}$ M huC242-SPDB-DM4, in the presence of 30 µM chloroquine, 30 nM BafA1, or no treatment.

Figure 8:
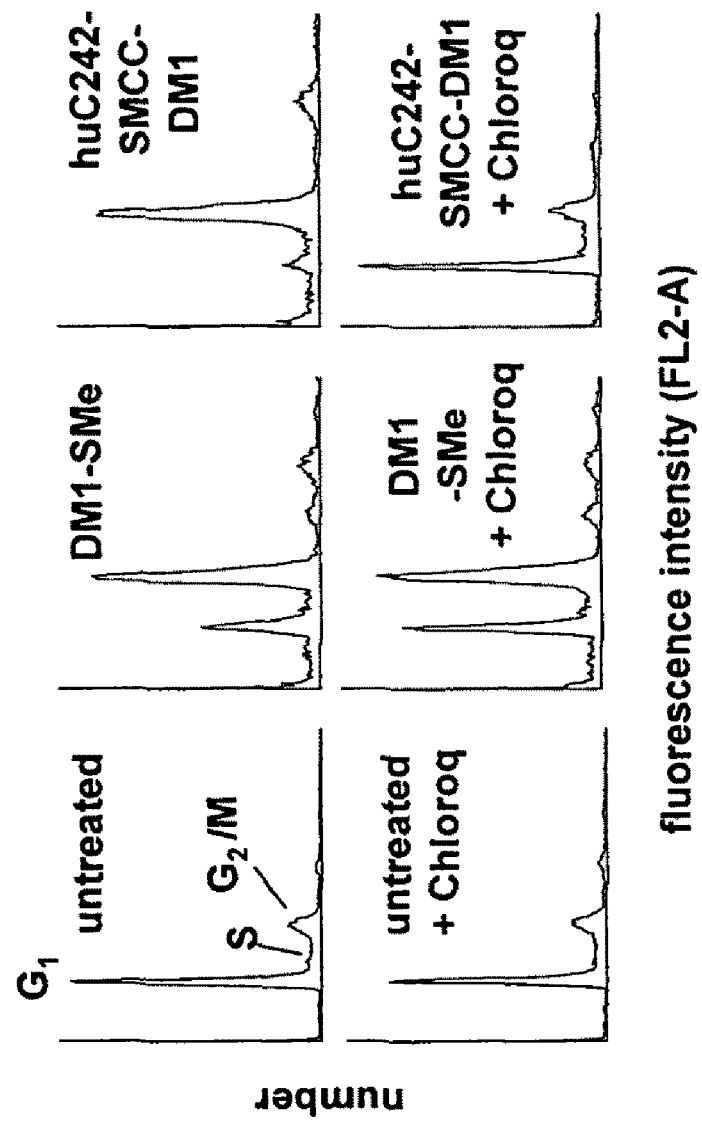

FIG. 8. Effects of chloroquine on the mitotic arrest induced by huC242-SMCC-DM1. FACS histograms (FL2-A) display DNA contents of samples of asynchronous, exponentially growing COLO 205 cells either untreated or treated for 20 h with $10^{-8}$ M DM1-SMe, $3\times10^{-9}$ M huC242-SMCC-DM1, in the presence or absence of 30 µM chloroquine. In the presence of chloroquine, $G_2/M$ arrest induced by huC242-SMCC-DM1 was almost completely abrogated (14% in $G_2$), whereas chloroquine had only a modest effect on $G_2/M$ arrest caused by DM 1-SMe (51% in $G_2$).

Figure 9:
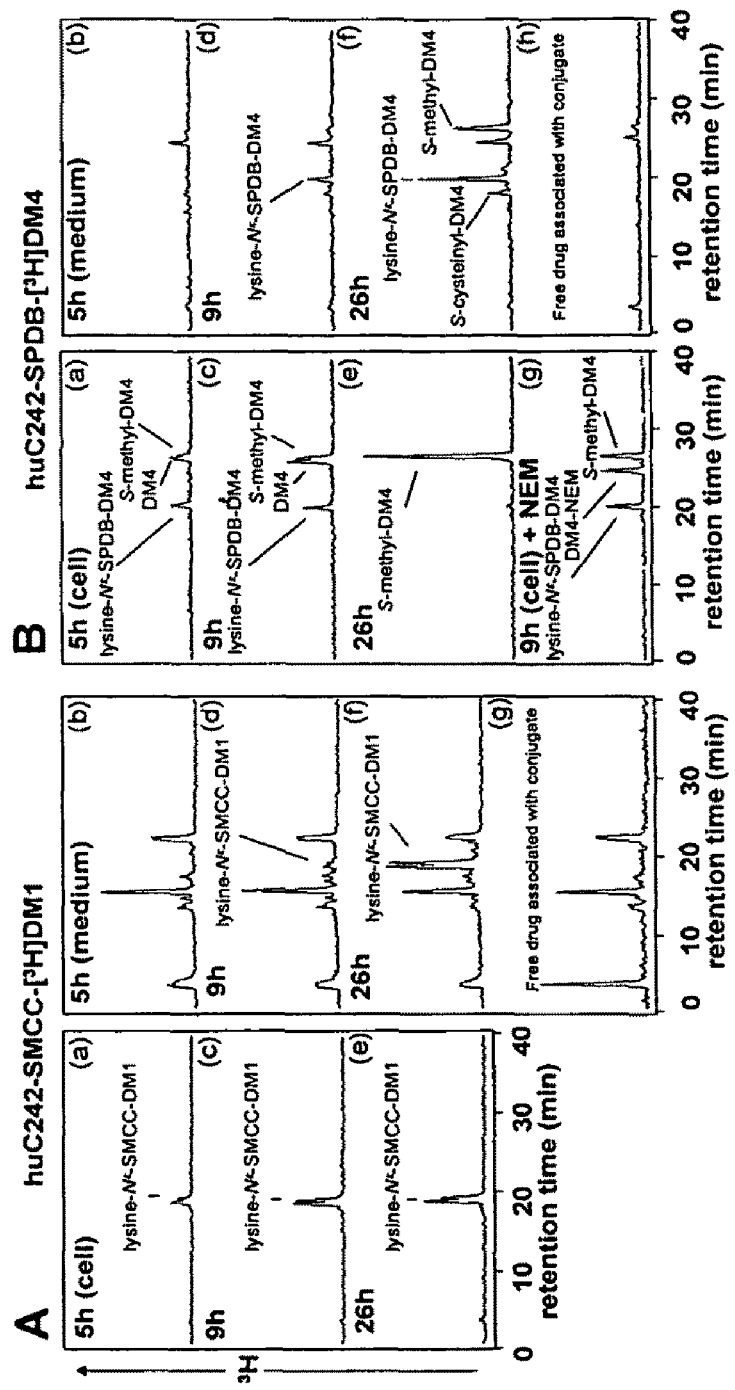

FIG. 9. Maytansinoid metabolites formed upon treatment of COLO 205 cells with huC242-SMCC-[³H]DM1 (A) or huC242-SPDB-[³H]DM4 (B). Metabolites were extracted with acetone from the cell pellet and the spent media, respectively, and then analyzed by HPLC. The effluent from the column was monitored for tritium using an in-line flow scintillation analyzer with an output in $mV^2$; thus the chromatograms show retention time on the abscissa and $mV^2$ as a measure of [³H] on the ordinate. Panels a-f are the chromatograms associated with the medium and cell pellets from COLO 205 cells that were treated for 5, 9 and 26 hours with huC242-SMCC-[³H]DM1 (A) or huC242-SPDB-[³H]DM4 (B). Panel g from (A) and panel h (B) are the chromatograms obtained from the acetone extract of the huC242-SMCC-[³H]DM1 and huC242-SPDB-[3H]DM4 conjugate sample, respectively, used in the experiment. The chromatogram in panel g (B) is derived from cells that were treated equally to the cell pellet from the 9-h incubation (as in panel c), except that the sample was additionally exposed to NEM before chromatography to alkylate any sulfhydryl groups.

Figure 10:
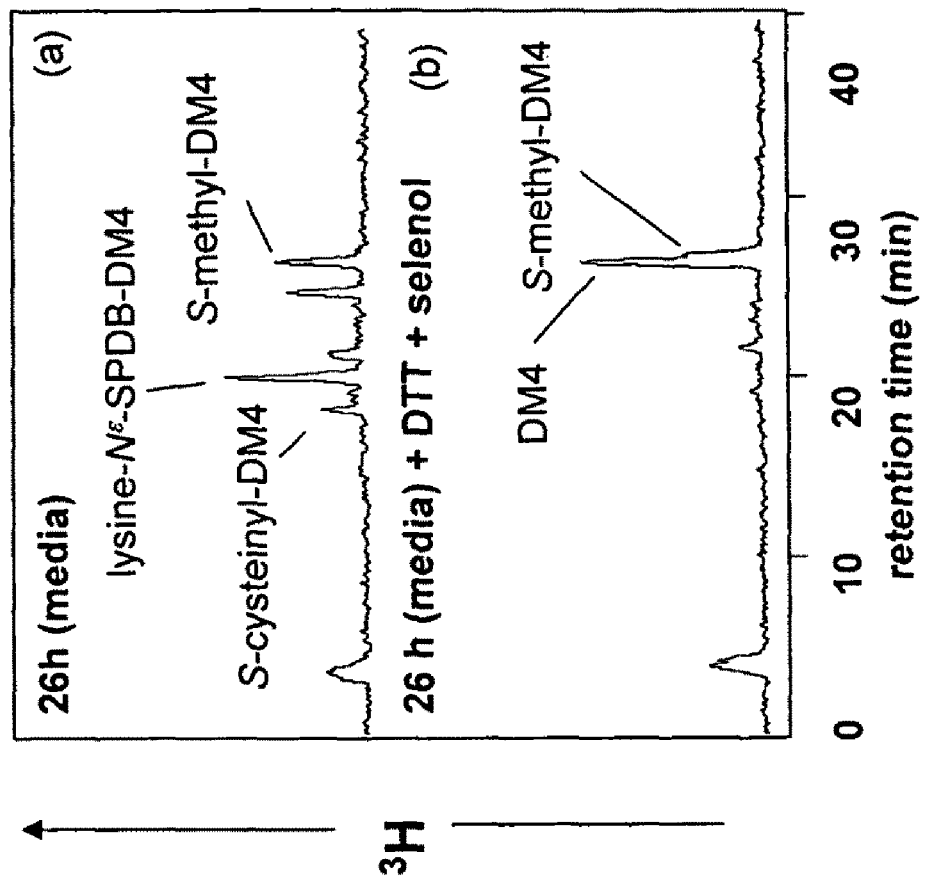

FIG. 10 Treatment of metabolites in the medium from COLO 205 cells treated with huC242-SPDB-[³H]DM4 with DTT and selenol. Metabolites were extracted with acetone from the spent media following a 26-h exposure of cells to conjugate. The extract was divided into two equal portions. One portion was subjected directly to chromatography (a) and the other portion (b) was treated with DTT and selenol before chromatography to reduce all disulfide bonds. The effluent from the column was monitored for tritium using an in-line flow scintillation analyzer with an output in $mV^2$; thus the chromatograms show retention time on the abscissa and $mV^2$ as a measure of [³H] on the ordinate.

Figure 11:
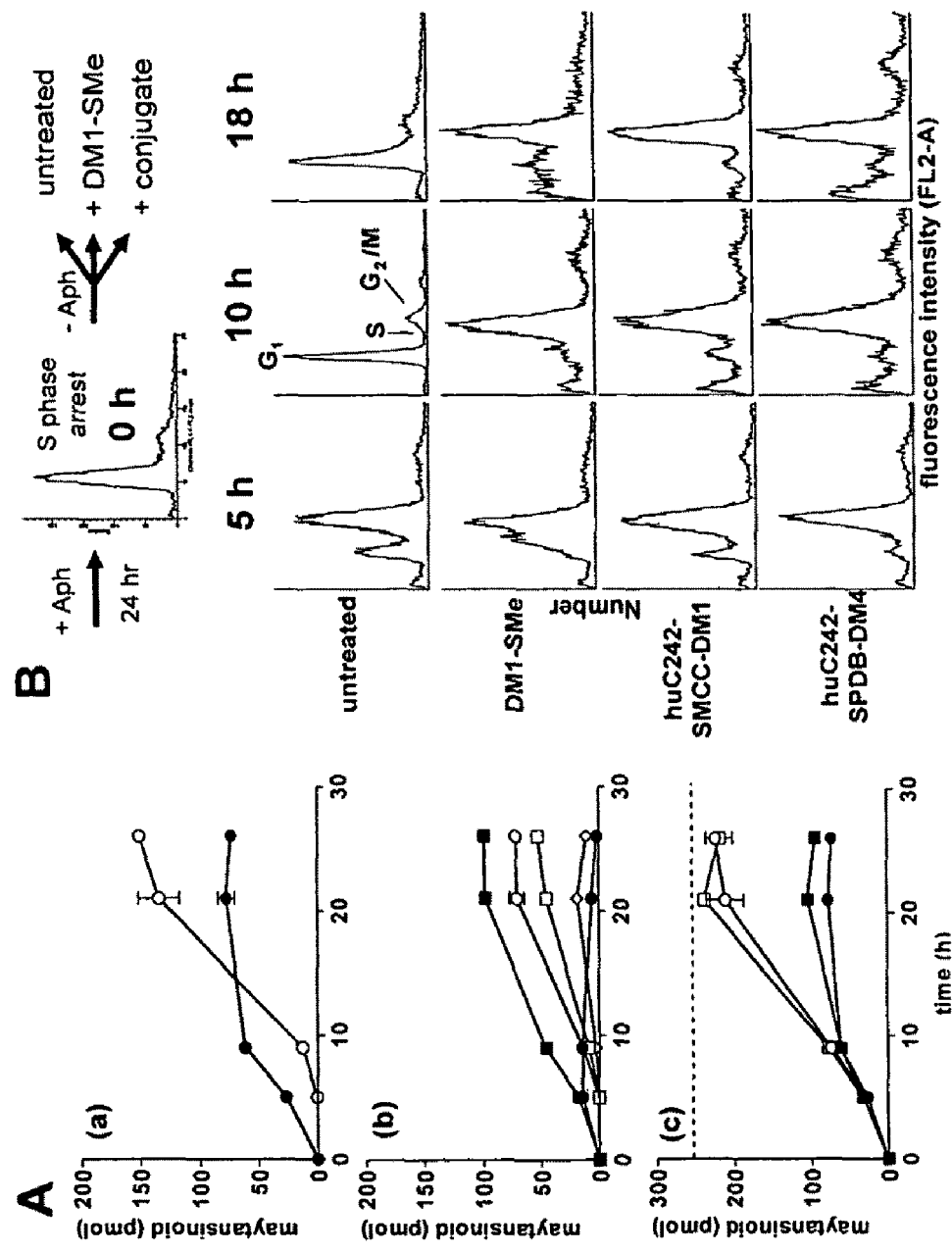

FIG. 11. Accumulation of maytansinoid metabolites inside and outside of COLO 205 cells treated with [³H] conjugates and their correlation with mitotic arrest. (A) The areas associated with the peaks of radioactivity for the metabolites in FIG. 9 were quantified and converted to pmol as described in Materials and Methods, Example 2 Panels a-c show the changes in the amount of various metabolites in the samples over a 26-h incubation period. Panel a: Accumulation of lysine-$N^\epsilon$-SMCC-DM1 in the media (open circles) and cells (closed circles) following treatment of COLO 205 cells with huC242-SMCC-[³H]DM1. Panel b: Changes in the amounts of maytansinoid metabolites in the cell pellet (closed symbols) and in the media (open symbols) following treatment of COLO 205 with huC242-SPDB-[³H]DM4: S-methyl-DM4 (squares), lysine-$N^\epsilon$-SPDB-DM4 (circles), S-cysteinyl-DM4 (diamonds). Panel c: Change of the sum of all metabolites present for both conjugates, huC242-SMCC-[³H]DM1 (circles) and huC242-SPDB-[³H]DM4 (squares), either in the cell pellet (solid symbols) or in the cell pellet and medium together (open symbols). (B) COLO 205 cells were synchronized in S phase with a 24 h treatment of 2 µg/mL aphidicolin. The cells were released from S phase by the removal of aphidicolin and incubated with $10^{-8}$ M DM1-SMe, $3\times10^{-9}$ M huC242-SMCC-DM1, $3\times10^{-9}$ M huC242-SPDB-DM4, or left untreated FACS analysis was performed at 5, 10, and 18 h after aphidicolin release.

Figure 12:
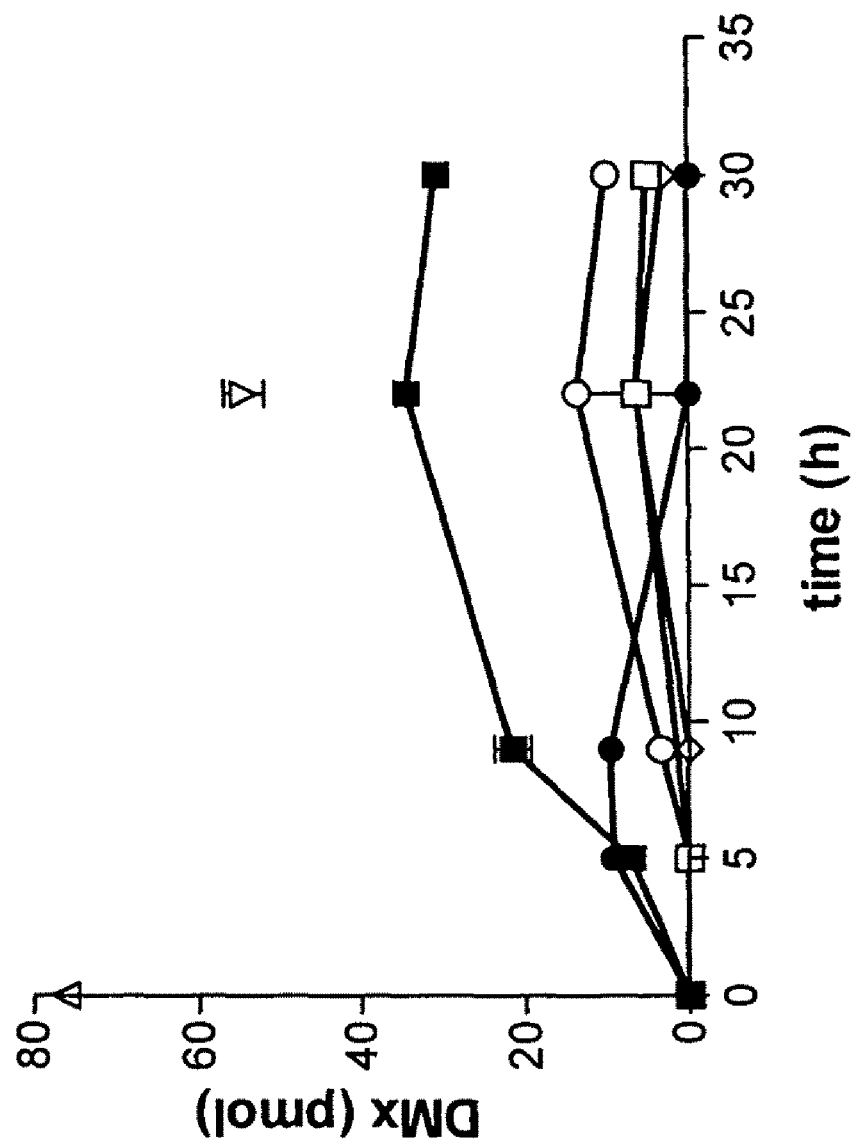

FIG. 12 Generation of maytansinoid metabolites from cell surface-bound huC242-SPDB-[³H]DM4. Proliferating COLO 205 cells were placed on ice and incubated with a saturating amount of huC242-SPDB-[³H]DM4 ($10^{-7}$ M) to allow the conjugate to bind to the surface receptors without being internalized. The cells were then washed, and the amount of bound radioactivity was quantified by subjecting small fractions of the samples to scintillation counting. The total amount of radioactivity associated with the cell sample after conjugate binding at 0° C. is shown on the ordinate at T=0 (open triangle, 78 pmol) and after 22 hours of incubation (open triangle, 57 pmol). The curves show the accumulation of various metabolites in the cells (closed symbols) and in the medium (open symbols) for samples incubated for 5, 9, 22, and 30 hours. Maytansinoid metabolites are S-methyl-DM4 (squares), lysine-$N^\epsilon$-SPDB-DM4 (circles), and S-cysteinyl-DM4 (diamonds).

Figure 13:
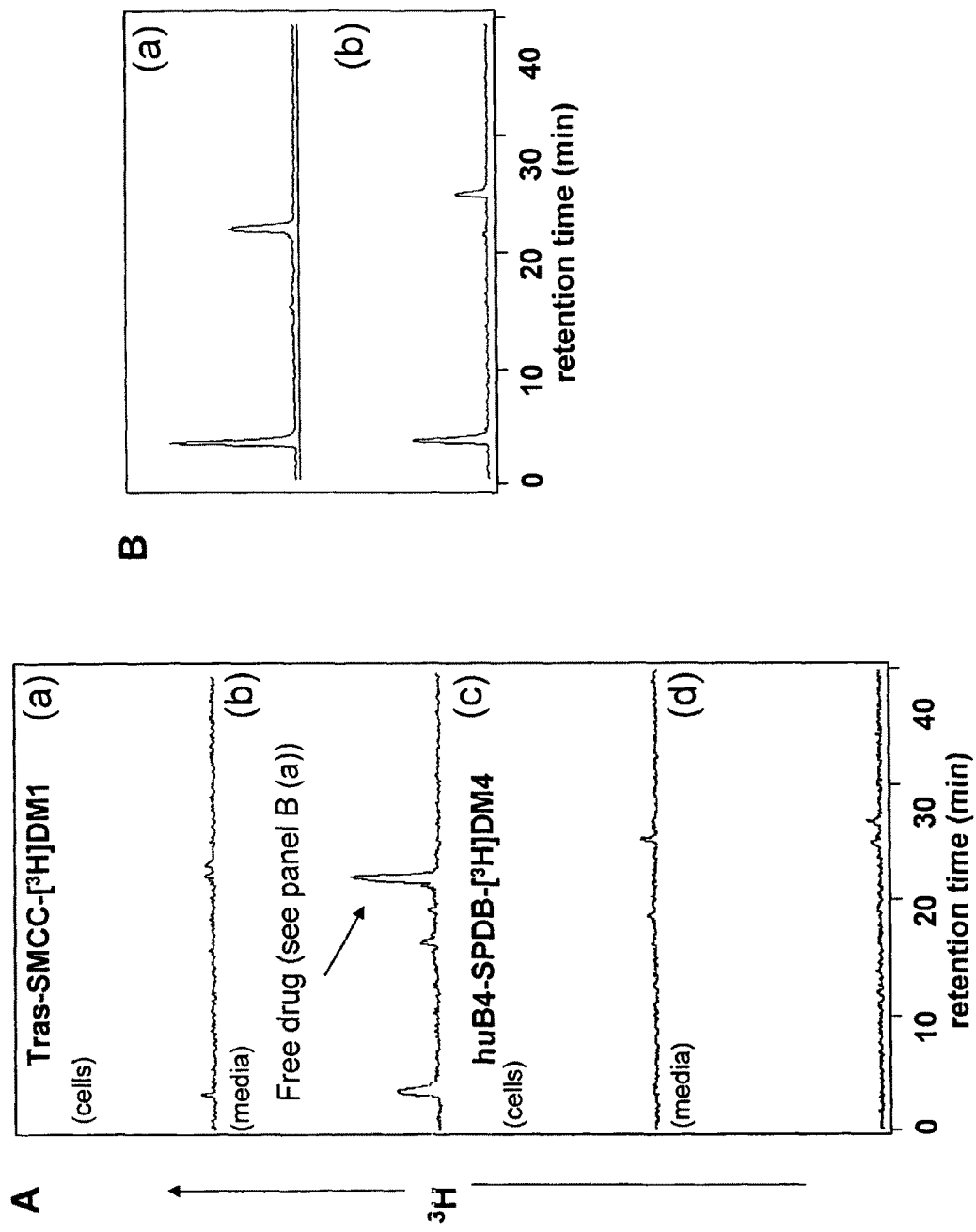

FIG. 13. Antigen dependence of cellular metabolism. Maytansinoid metabolites were studied with conjugates that do not bind to COLO 2005 cells. Panel A (a,b) shows chromatograms of acetone extracts of cells (a) and medium (b) after treatment of COLO 205 cells for 26 hours with Tras-SMCC-[³H]DM1. Correspondingly, Panel A (c) (cells) and d (medium) are for the conjugate huB4-SPDB-[³H]DM4. Panel B shows chromatograms associated with acetone extracts of Tras-SMCC-[³H]DM1 (a) and huB4-SPDB-[³H]DM4 (b).

Figure 14:
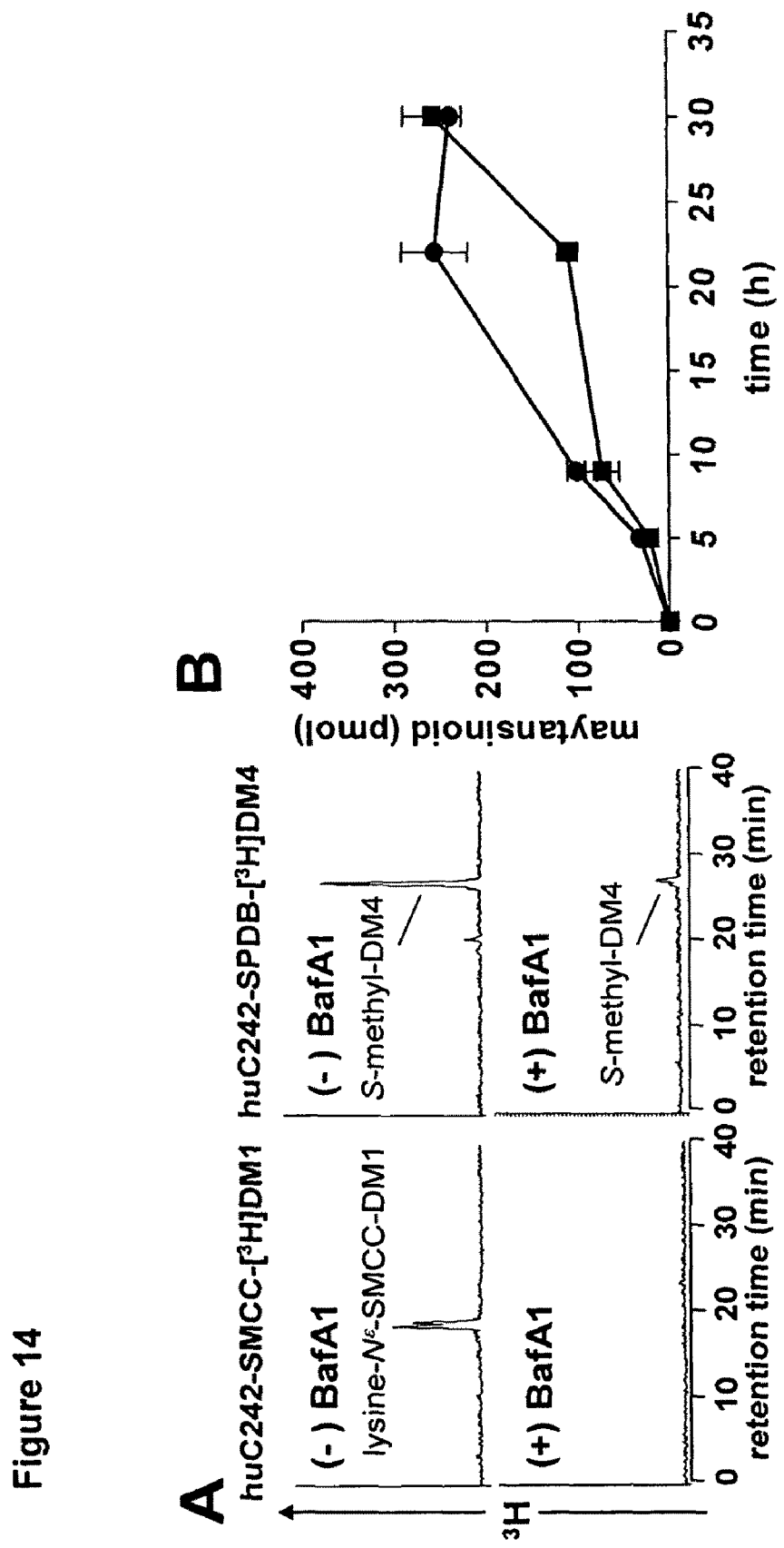

FIG. 14. The role of the major metabolites in cellular toxicity. (A) Influence of BafA1 on the cellular metabolism of huC242-SMCC-[³H]DM1 and huC242-SPDB-[³H]DM4 in the presence or absence of BafA1. The chromatograms are from acetone extracts of COLO 205 cells treated with huC242-SMCC-[³H]DM1 or huC242-SPDB-[³H]DM4 for 22 h, in the presence of BafA1 or no treatment. (B) Accumulation of maytansinoid metabolites formed upon treatment of COLO 205 cells with huC242-SPDB-D-[³H]DM4 vs. huC242-SPDB-[³H]DM4. Total amounts of maytansinoid metabolites generated from huC242-SPDB-D-[³H]DM4 (closed squares) and from huC242-SPDB-[³H]DM4 (closed circles). The metabolites were quantified as described in FIG. 9.

Figure 15:
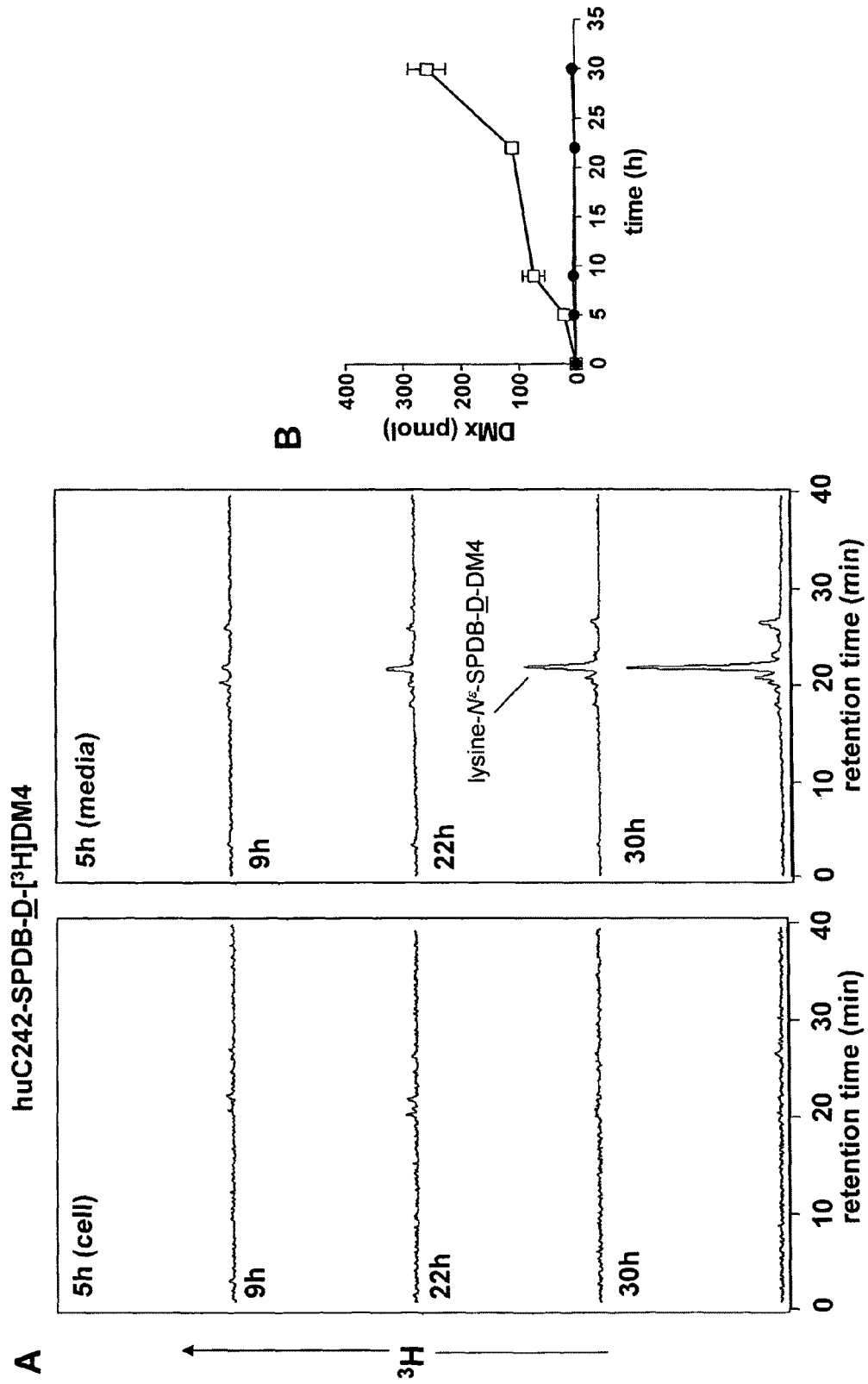

FIG. 15 Maytansinoid metabolites formed upon treatment of COLO 205 cells with huC242-SPDB-D-[³H]DM4. COLO 205 cells were treated with huC242-SPDB-D-[³H]DM4 and cells and media were harvested at 5, 9, 22, and 30 h and analyzed for metabolites as described in FIG. 7. (A) The Left Panels show the chromatograms of the cell extracts at the four consecutive time points, and the Right Panels represent the chromatograms of the corresponding medium samples. (B) Total amounts of maytansinoid metabolites generated from huC242-SPDB-D-[³H]DM4 in the cells (closed circles) and from medium (open squares) were quantified as described in FIG. 9.

Figure 16:
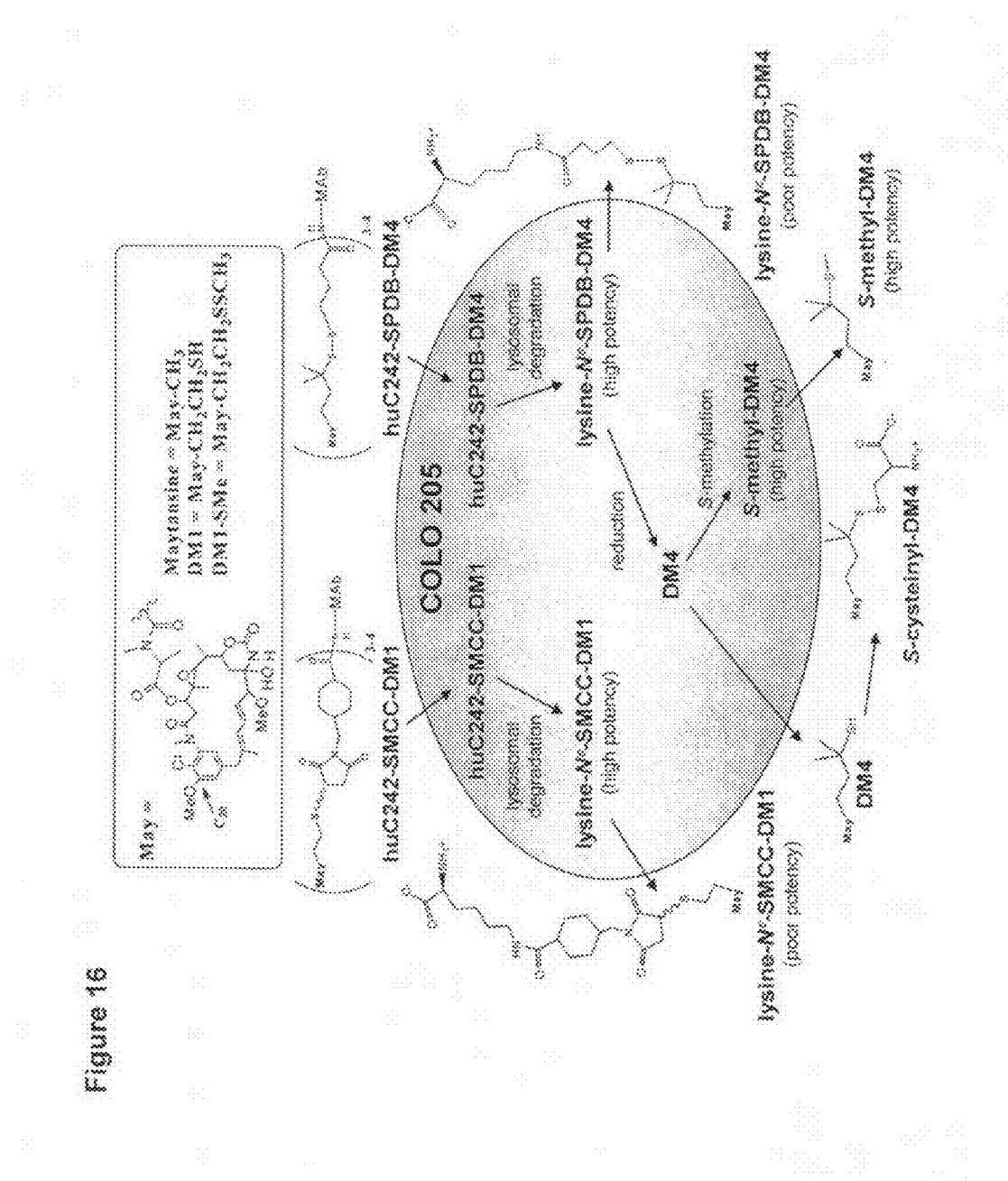

FIG. 16. Model for the activation of huC242-maytansinoid in targeted cancer cells. The initial steps of conjugate activation are similar for the disulfide-linked conjugate, huC242-SPDB-DM4, and the non-disulfide-linked conjugate, huC242-SMCC-DM1. Both are first internalized by the target cancer cells via antigen-mediated endocytosis, delivered to lysosomes by the vesicular trafficking, and then degraded into the lysine-derivatives, lysine-$N^\epsilon$-SMCC-DM1 and lysine-$N^\epsilon$-SPDB-DM4. These lysine-derivatives likely bind to the intracellular target, tubulin, and cause cytotoxicity by the inhibition of microtubule polymerization. Unlike lysine-$N^\epsilon$-SMCC-DM1, the lysine-$N^\epsilon$-SPDB-DM4 can undergo further intracellular modifications, reduction and S-methylation, ultimately leading to the formation of S-methyl-DM4. Whereas the charged lysine-derivatives are no longer active once they leave the targets cells, the neutral lipophilic S-methyl-DM4 compound continues to be active and can reenter the target cells or enter neighboring cells (bystander).

FIG. 17. Scheme showing the synthesis of thiomethyl maytansinoids.

DETAILED DESCRIPTION OF THE INVENTION

The inventors have unexpectedly found that if a drug undergoes alkylation (e.g., methylation) at a thiol group once the drug is released from the conjugate, the alkylation provides protection to the drug from reacting with cellular molecules having a sulfhydryl group, like cysteine, or proteins (e.g., plasma albumin), or disulfide group, such as cystine, oxidized glutathione, which would hinder or inactivate the free drug. Further, the inventors have unexpectedly discovered that the potency of a drug in a cell binding agent-drug conjugate is dependant on the hindrance provided at the linkage between a cytotoxic drug and a cell-binding agent. The conjugate is hindered by adding alkyl groups, such as methyl groups, which are attached to the two α-carbons next to the disulfide bond. The hindrance, if provided on the drug side of the conjugate, induces alkylation (e.g., methylation) of the free drug, once the drug is released at its target, which could be intra- or extra-cellular. Preparation of Sterically Hindered Thiol and Disulfide-Containing Maytansinoids, which bear one or two alkyl substituents on the α-carbon atom bearing the sulfur atom are described in U.S. patent publication No. 2004/0235840, published Nov. 25, 2004, which is incorporated herein in its entirety by reference.

Thus, in one embodiment, when the disulfide bond is cleaved in the cell binding agent-drug conjugate, it releases the drug within or in the vicinity of the targeted cell. Furthermore, the drug undergoes alkylation (e.g., methylation or the addition of one or more $CH_3$ groups) at the thiol group, which makes the drug stable and potent to kill not only the targeted cell but also a non-targeted cell, or cells that are surrounding the targeted cell in a heterogeneous or mixed cell population present in, for example, a tumor.

The hindered thiol group in a cell binding agent-drug conjugate provides advantage over the non-hindered thiol groups in a similar conjugate because, unlike the unhindered thiol group, it more readily undergoes alkylation upon drug cleavage which prevents the drug from undergoing a modification reaction that would result in loss of its functionality. Moreover, the alkylated drug is potent over a period of time and is capable of targeting a neighboring cell in a tumor to thereby kill the neighboring cell. The potent alkylated form of drug can be chemically synthesized as shown in the examples, and was found to be at least 100-fold more potent in vitro.

This invention also provides an improved method for targeting cells in mixed or heterogeneous cell populations, especially cells that are to be destroyed, such as tumor cells (particularly solid tumor cells), virus infected cells, microorganism infected cells, and parasite infected cells, which are comprised of a heterogeneous or mixed population of abnormal cells.

The conjugate used in the inventive method has one or more maytansinoids, taxanes or CC-1065 analogs, linked to a cell-binding agent via a disulfide linker. In one method of making the conjugate, a cell-binding agent, for example an antibody, is first modified with a heterobifunctional cross-linking reagent such as SPP, SPDP, SPDB, SSNPB, or SSNPP. The cross-linking reagents listed all use N-hydroxysuccinimide ester chemistry for the reaction with the antibody. The compounds listed vary in chain length and degree of hindrance around the dithiopyridine that reacts with a free thiol. In a second step, the modified agent is reacted with a drug, for example, a maytansinoid, a taxane or a CC-1065 analog having a thiol group to produce the cell-binding agent drug conjugate. Therefore, the final linker is assembled from two pieces, the cross-linking reagent introduced into the cell-binding agent and the sulfhydryl group from the drug such as in DM1 or DM4. Alternatively, the drug, such as a maytansinoid, can be modified with a cross-linking reagent before being reacted with a cell-binding agent. See, for example, U.S. Pat. No. 6,441,163 B1.

Although alkylation upon drug cleavage is the preferred event and it is possible for one of skilled in the art to isolate the in vivo alkylated maytansinoids (e.g., in vivo methylated maytansinoids), the maytansinoids can also be alkylated in vitro as shown in FIG. 8. The in vitro methylated maytansinoids are highly potent in killing tumor cells.

Cell-Binding Agents

The effectiveness of the compounds of the invention as therapeutic agents depends on the careful selection of an appropriate cell-binding agent. Cell-binding agents may be of any kind presently known, or that become known and include peptides and non-peptides. Generally, these can be antibodies (especially monoclonal antibodies and fragments thereof), lymphokines, hormones, growth factors, vitamins, nutrient-transport molecules (such as transferrin), or any other cell-binding molecule or substance that specifically binds a target.

The target is generally present on the tumor but not necessarily on the cell surface of the tumor cells, for example, the target may also initially be present on the cell surface and detach to be shed into the surrounding medium.

More specific examples of cell-binding agents that can be used include:

polyclonal and monoclonal antibodies, including fully human antibodies; single chain antibodies (polyclonal and monoclonal);

fragments of antibodies (polyclonal and monoclonal) such as Fab, Fab', F(ab')$_2$, and Fv (Parham, 131 J. Immunol. 2895-2902 (1983); Spring et al., 113 J. Immunol. 470-478 (1974); Nisonoff et al., 89 Arch. Biochem. Biophys. 230-244 (1960));

chimeric antibodies and antigen-binding fragments thereof;

domain antibodies (dAbs) and antigen-binding fragments thereof, including camelid antibodies (Desmyter et al., 3 Nature Struct. Biol, 752, 1996);

shark antibodies called new antigen receptors (IgNAR) (Greenberg et al., 374 Nature, 168, 1995; Stanfield et al. 305 Science 1770-1773, 2004);

interferons (e.g. alpha, beta, gamma);

lymphokines such as IL-2, IL-3, IL-4, IL-6;

hormones such as insulin, TRH (thyrotropin releasing hormone), MSH (melanocyte-stimulating hormone), steroid hormones, such as androgens and estrogens;

growth factors and colony-stimulating factors such as EGF, TGF-alpha, FGF, VEGF, G-CSF, M-CSF and GM-CSF (Burgess, 5 Immunology Today 155-158 (1984));

transferrin (O'Keefe et al., 260 J. Biol. Chem. 932-937 (1985)); and vitamins, such as folate.

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of antibody fragments, such as Fab and scFv (single chain variable region), specifically human scFv (see e.g., Griffiths et al., U.S. Pat. Nos. 5,885,793 and 5,969,108; McCafferty et al., WO 92/01047; Liming et al., WO 99/06587). In addition, resurfaced antibodies disclosed in U.S. Pat. No. 5,639,641 may also be used, as may humanized antibodies.

Selection of the appropriate cell-binding agent is a matter of choice that depends upon the particular cell population that is to be targeted, but in general human monoclonal antibodies are preferred if an appropriate one is available.

For example, the monoclonal antibody J5 is a murine IgG2a antibody that is specific for Common Acute Lymphoblastic Leukemia Antigen (CALLA) (Ritz et al, 283 Nature 583-585 (1980)) and can be used if the target cells express CALLA such as in the disease of acute lymphoblastic leukemia.

The monoclonal antibody MY9 is a murine IgG$_1$ antibody that binds specifically to the CD33 antigen (J. D. Griffin et al 8 Leukemia Res., 521 (1984)) and can be used if the target cells express CD33 as in the disease of acute myelogenous leukemia (AML).

Similarly, the monoclonal antibody anti-B4 interchangeably also called B4, is a murine IgG$_1$ that binds to the CD19 antigen on B cells (Nadler et al, 131 J. Immunol. 244-250 (1983)) and can be used if the target cells are B cells or diseased cells that express this antigen such as in non-Hodgkin's lymphoma or chronic lymphoblastic leukemia. Also, N901, which is murine monoclonal antibody that binds to the CD56 (neural cell adhesion molecule) antigen found on cells of neuroendocrine origin, including small cell lung tumor, can be used. These antibodies are preferably resurfaced or humanized prior to their use. For example, a resurfaced or humanized MY9, anti-B4 or N901 is a preferred antibody in the drug-antibody conjugate. Resurfacing or humanization of these antibodies is described in Roguska et al. Proc Natl Acad Sci USA. 1994 Feb. 1; 91(3):969-73, which is incorporated herein by reference.

In addition, the monoclonal antibody C242 that binds to the CanAg antigen (U.S. Pat. No. 5,552,293) can be used to treat CanAg expressing tumors, such as colorectal, pancreatic, non-small cell lung, and gastric cancers. HuC242 is a humanized form of the monoclonal antibody C242 that is described in U.S. Pat. No. 5,552,293 and for which the hybridoma is deposited with the ECACC, identification Number 90012601. A humanized form can be prepared by either applying the CDR-grafting methodology (U.S. Pat. Nos. 5,585,089; 5,693,761; and 5,693,762) or the resurfacing methodology (U.S. Pat. No. 5,639,641). HuC242 can also be used to treat CanAg expressing tumors, such as colorectal, pancreatic, non-small cell lung, and gastric cancers.

Further, the antibody trastuzumab can be used to treat breast and other cancers, such as prostate and ovarian cancers that express the Her2 antigen.

Anti-IGF-IR antibodies that bind to insulin growth factor receptor are also useful.

Ovarian cancer and prostate cancer can be successfully targeted with, for example, an anti-MUC1 antibody, such as anti-HMFG-2 (Taylor-Papadimitriou et al., 28. Int. J. Cancer 17-21, 1981) or hCTM01 (56 Cancer Res. 5179-5185, 1996) or DS6 and an anti-PSMA (prostate-specific membrane antigen), such as J591 (Liu et al. 57 Cancer Res. 3629-3634, 1997) respectively.

Non-antibody molecules can also be used to target specific cell populations. For example, GM-CSF, which binds to myeloid cells, can be used as a cell-binding agent to target diseased cells from acute myelogenous leukemia. In addition, IL-2, which binds to activated T-cells, can be used for prevention of transplant graft rejection, for therapy and prevention of graft-versus-host disease, and for treatment of acute T-cell leukemia. MSH, which binds to melanocytes, can be used for the treatment of melanoma. Folic acid can be used to target the folate receptor expressed on ovarian and other tumors. Epidermal growth factor (EGF) can be used to target squamous cancers such as lung and head and neck. Somatostatin can be used to target neuroblastomas and other tumor types. Cancers of the breast and testes can be successfully targeted with estrogen (or estrogen analogues) or androgen (or androgen analogues) respectively as cell-binding agents.

Cross-Linking Reagents

As used herein, a "linker" is any chemical moiety that links a cell-binding agent covalently to a drug, such as a maytansinoid, a taxane, or a CC1065 analog. Part of the linker is provided by the drug. For example, DM1, a thiol-containing maytansinoid, is a derivative of maytansine. To form DM1, the side chain at the C-3 hydroxyl group of maytansine is modified to have a free SH. This thiolated form of maytansine is able to react with a modified cell-binding agent to form a conjugate. Therefore, the final linker is assembled from two pieces, part from the cross-linking reagent introduced into the cell-binding agent and part from the side chain from the DM 1.

Cleavable linkers are linkers that can be cleaved under mild conditions, i.e. conditions under which the activity of the drug, such as maytansinoids, taxanes or CC1065, is not affected and conditions that are present inside a cell. Many known linkers fall in this category and are described below.

Disulfide containing linkers are linkers cleavable through disulfide exchange, which can occur under physiological conditions.

Acid-labile linkers are linkers cleavable at acid pH. For example, certain intracellular compartments, such as endosomes and lysosomes, have an acidic pH (pH 4-5), and provide conditions suitable to cleave acid-labile linkers.

Linkers that are photo-labile are useful at the body surface and in many body cavities that are accessible to light. Furthermore, infrared light can penetrate tissue.

Some linkers can be cleaved by peptidases. Only certain peptides are readily cleaved inside or outside cells, see e.g. Trouet et al., 79 Proc. Natl. Acad. Sci. USA, 626-629 (1982) and Umemoto et al. 43 Int. J. Cancer, 677-684 (1989).

Cytotoxic Agents

The cytotoxic agent used in the cytotoxic conjugate of the present invention may be any compound that results in the death of a cell, or induces cell death, or in some manner decreases cell viability. Preferred cytotoxic agents include, for example, maytansinoids and maytansinoid analogs, taxoids, CC-1065 and CC-1065 analogs, dolastatin and dolastatin analogs, defined below. These cytotoxic agents are conjugated to the antibodies, antibodies fragments, functional equivalents, improved antibodies and their analogs as disclosed herein The cytotoxic conjugates may be prepared by in vitro methods. In order to link a drug or prodrug to the antibody, a disulfide group is used. Conjugates can be constructed using a disulfide exchange reaction between the antibody and the drug or prodrug.

Maytansinoids

Among the cytotoxic agents that may be used in the present invention to form a cytotoxic conjugate, are maytansinoids and maytansinoid analogs. Examples of suitable maytansinoids include maytansinol and maytansinol analogs. Maytansinoids are drugs that inhibit microtubule formation and that are highly toxic to mammalian cells.

Examples of suitable maytansinol analogues include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

Specific examples of suitable analogues of maytansinol having a modified aromatic ring include:
(1) C-19-dechloro (U.S. Pat. No. 4,256,746) (prepared by LAH reduction of ansamytocin P2);
(2) C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and
(3) C-20-demethoxy, C-20-acyloxy (—OCOR), +/−dechloro (U.S. Pat. No. 4,294,757) (prepared by acylation using acyl chlorides).

Specific examples of suitable analogues of maytansinol having modifications of other positions include:
(1) C-9-SH (U.S. Pat. No. 4,424,219) (prepared by the reaction of maytansinol with $H_2S$ or $P_2S_5$);
(2) C-14-alkoxymethyl (demethoxy/$CH_2OR$) (U.S. Pat. No. 4,331,598);
(3) C-14-hydroxymethyl or acyloxymethyl ($CH_2OH$ or $CH_2OAc$) (U.S. Pat. No. 4,450,254) (prepared from *Nocardia*);
(4) C-15-hydroxy/acyloxy (U.S. Pat. No. 4,364,866) (prepared by the conversion of maytansinol by *Streptomyces*);
(5) C-15-methoxy (U.S. Pat. Nos. 4,313,946 and 4,315,929) (isolated from *Trewia nudiflora*);
(6) C-18-N-demethyl (U.S. Pat. Nos. 4,362,663 and 4,322,348) (prepared by the demethylation of maytansinol by *Streptomyces*); and
(7) 4,5-deoxy (U.S. Pat. No. 4,371,533) (prepared by the titanium trichloride/LAH reduction of maytansinol).

In a preferred embodiment, the cytotoxic conjugates of the present invention utilize the thiol-containing maytansinoid DM1, formally termed $N^{2'}$-deacetyl-$N^{2'}$-(3-mercapto-1-oxopropyl)-maytansine, as the cytotoxic agent. DM1 is represented by the following structural formula (I):

(I)

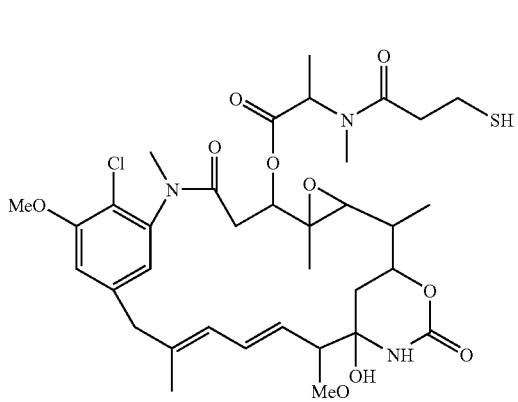

In another preferred embodiment, the cytotoxic conjugates of the present invention utilize the thiol-containing maytansinoid DM4 formally termed N$^{2'}$-deacetyl-N-$^{2'}$(4-methyl-4-mercapto-1-oxopentyl)-maytansine as the cytotoxic agent. DM4 is represented by the following structural formula (II):

(II)

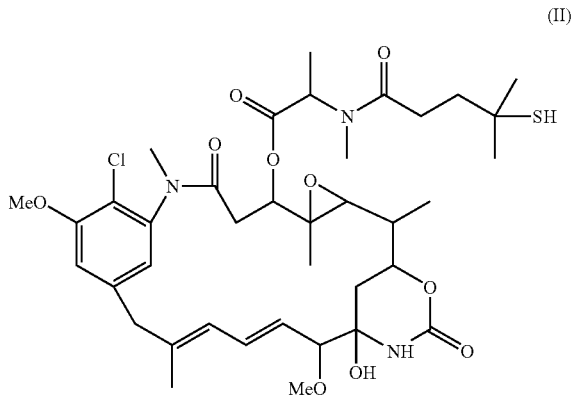

In further preferred embodiments of the invention, other maytansines, including thiol and disulfide-containing maytansinoids bearing a mono or di-alkyl substitution on the carbon atom bearing the sulfur atom, may be used. These include a maytansinoid having, at C-3, C-14 hydroxymethyl, C-15 hydroxy, or C-20 desmethyl, an acylated amino acid side chain with an acyl group bearing a hindered sulfhydryl group, wherein the carbon atom of the acyl group bearing the thiol functionality has one or two substituents, said substituents being CH$_3$, C$_2$H$_5$, linear or branched alkyl or alkenyl having from 1 to 10 carbon atoms, cyclic alkyl or alkenyl having from 3 to 10 carbon atoms, phenyl, substituted phenyl, or heterocyclic aromatic or heterocyclic radical, and further wherein one of the substituents can be H, and wherein the acyl group has a linear chain length of at least three carbon atoms between the carbonyl functionality and the sulfur atom.

Such additional maytansines include compounds represented by formula (III):

(III)

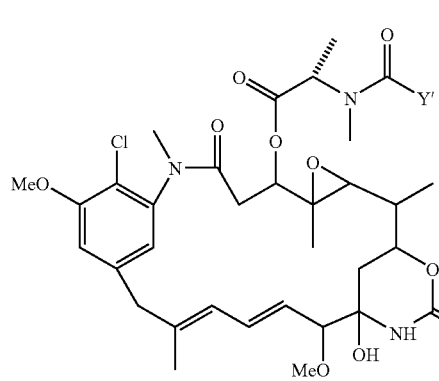

wherein:
Y' represents
$(CR_7R_8)_l(CR_9=CR_{10})_pP(C\equiv C)_qA_o(CR_5R_6)_mD_u$
$(CR_{11}=CR_{12})_r$
$(C\equiv C)_sB_t(CR_3R_4)_nCR_1R_2SZ$,
wherein:
R$_1$ and R$_2$ are each independently linear alkyl or alkenyl having from 1 to 10 carbon atoms, such as CH$_3$ and C$_2$H$_5$, branched or cyclic alkyl or alkenyl having from 3 to 10 carbon atoms, phenyl, substituted phenyl or heterocyclic aromatic or heterocyclic radical, and in addition R$_2$ can be H;

A, B, D are cycloalkyl or cycloalkenyl having 3-10 carbon atoms, simple or substituted aryl or heterocyclic aromatic or heterocyclic radical;

R$_3$, R$_4$, R$_5$, R$_6$, R$_7$, R$_8$, R$_9$, R$_{10}$, R$_{11}$, and R$_{12}$ are each independently H, linear alkyl or alkenyl having from 1 to 10 carbon atoms, such as CH$_3$ and C$_2$H$_5$, branched or cyclic alkyl or alkenyl having from 3 to 10 carbon atoms, phenyl, substituted phenyl or heterocyclic aromatic or heterocyclic radical;

l, m, n, o, p, q, r, s, t and u are each independently 0 or an integer of from 1 to 5, provided that at least two of l, m, n, o, p, q, r, s, t and u are not zero at any one time; and Z is H, SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical.

Preferred embodiments of formula (III) include compounds of formula (III) wherein:
R$_1$ is methyl, R$_2$ is H and Z is H.
R$_1$ and R$_2$ are methyl and Z is H.
R$_1$ is methyl, R$_2$ is H, and Z is —SCH$_3$.
R$_1$ and R$_2$ are methyl, and Z is —SCH$_3$.

Such additional maytansines also include compounds represented by formula (IV-L), (IV-D), or (IV-D,L):

(IV-L)

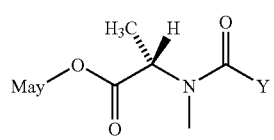

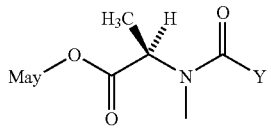
(IV-D)

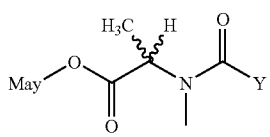
(IV-D,L)

wherein:

Y represents $(CR_7R_8)_l(CR_5R_6)_m(CR_3R_4)_nCR_1R_2SZ$, wherein:

$R_1$ and $R_2$ are each independently linear alkyl or alkenyl having from 1 to 10 carbon atoms, such as $CH_3$ and $C_2H_5$, branched or cyclic alkyl or alkenyl having from 3 to 10 carbon atoms, phenyl, substituted phenyl, or heterocyclic aromatic or heterocyclic radical, and in addition $R_2$ can be H;

$R_3$, $R_4$, $R_5$, $R_6$, $R_7$ and $R_8$ are each independently H, linear alkyl or alkenyl having from 1 to 10 carbon atoms, such as $CH_3$ and $C_2H_5$, branched or cyclic alkyl or alkenyl having from 3 to 10 carbon atoms, phenyl, substituted phenyl, or heterocyclic aromatic or heterocyclic radical;

l, m and n are each independently an integer of from 1 to 5, and in addition n can be 0;

Z is H, SR or —COR wherein R is linear or branched alkyl or alkenyl having from 1 to 10 carbon atoms, cyclic alkyl or alkenyl having from 3 to 10 carbon atoms, or simple or substituted aryl or heterocyclic aromatic or heterocyclic radical; and May represents a maytansinoid which bears the side chain at C-3, C-14 hydroxymethyl, C-15 hydroxy or C-20 desmethyl.

Preferred embodiments of formulas (IV-L), (IV-D) and (IV-D,L) include compounds of formulas (IV-L), (IV-D) and (IV-D,L) wherein:

$R_1$ is methyl, $R_2$ is H, $R_5$, $R_6$, $R_7$, and $R_8$ are each H, l and m are each 1, n is 0, and Z is H.

$R_1$ and $R_2$ are methyl, $R_5$, $R_6$, $R_7$, $R_8$ are each H, l and m are 1, n is 0, and Z is H.

$R_1$ is methyl, $R_2$ is H, $R_5$, $R_6$, $R_7$, and $R_8$ are each H, l and m are each 1, n is 0, and Z is —$SCH_3$.

$R_1$ and $R_2$ are methyl, $R_5$, $R_6$, $R_7$, $R_8$ are each H, l and m are 1, n is 0, and Z is —$SCH_3$.

Preferably the cytotoxic agent is represented by formula (IV-L).

Such additional maytansines also include compounds represented by formula (V):

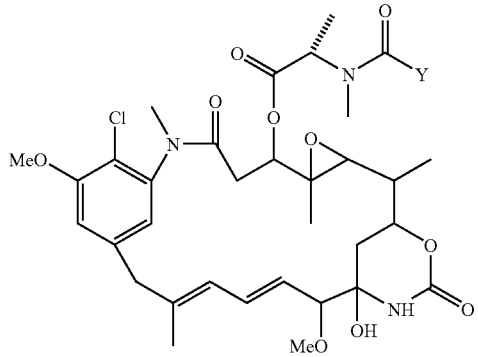
(V)

wherein:

Y represents $(CR_7R_8)_l(CR_5R_6)_m(CR_3R_4)_nCR_1R_2SZ$, wherein:

$R_1$ and $R_2$ are each independently linear alkyl or alkenyl having from 1 to 10 carbon atoms, such as $CH_3$ and $C_2H_5$, branched or cyclic alkyl or alkenyl having from 3 to 10 carbon atoms, phenyl, substituted phenyl or heterocyclic aromatic or heterocyclic radical, and in addition $R_2$ can be H;

$R_3$, $R_4$, $R_5$, $R_6$, $R_7$ and $R_8$ are each independently H, linear alkyl or alkenyl having from 1 to 10 carbon atoms, such as $CH_3$ and $C_2H_5$, branched or cyclic alkyl or alkenyl having from 3 to 10 carbon atoms, phenyl, substituted phenyl, or heterocyclic aromatic or heterocyclic radical;

l, m and n are each independently an integer of from 1 to 5, and in addition n can be 0; and Z is H, SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical.

Preferred embodiments of formula (V) include compounds of formula (V) wherein:

$R_1$ is methyl, $R_2$ is H, $R_5$, $R_6$, $R_7$, and $R_8$ are each H; l and m are each 1; n is 0; and Z is H.

$R_1$ and $R_2$ are methyl; $R_5$, $R_6$, $R_7$, $R_8$ are each H, l and m are 1; n is 0; and Z is H.

$R_1$ is methyl, $R_2$ is H, $R_5$, $R_6$, $R_7$, and $R_8$ are each H, l and m are each 1, n is 0, and Z is —$SCH_3$.

$R_1$ and $R_2$ are methyl, $R_5$, $R_6$, $R_7$, $R_8$ are each H, l and m are 1, n is 0, and Z is —$SCH_3$.

Such additional maytansines further include compounds represented by formula (VI-L), (VI-D), or (VI-D,L):

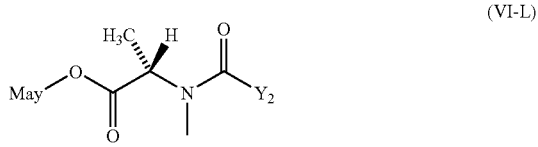
(VI-L)

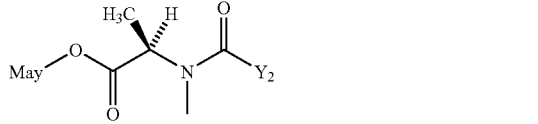
(VI-D)

-continued

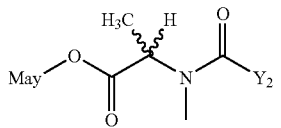
(VI-D,L)

wherein:
$Y_2$ represents $(CR_7R_8)_l(CR_5R_6)_m(CR_3R_4)_nCR_1R_2SZ_2$,
wherein:

$R_1$ and $R_2$ are each independently linear alkyl or alkenyl having from 1 to 10 carbon atoms, such as $CH_3$ and $C_2H_5$, branched or cyclic alkyl or alkenyl having from 3 to 10 carbon atoms, phenyl, substituted phenyl or heterocyclic aromatic or heterocyclic radical, and in addition $R_2$ can be H;

$R_3$, $R_4$, $R_5$, $R_6$, $R_7$ and $R_8$ are each independently H, linear cyclic alkyl or alkenyl having from 1 to 10 carbon atoms, such as $CH_3$ and $C_2H_5$, branched or cyclic alkyl or alkenyl having from 3 to 10 carbon atoms, phenyl, substituted phenyl or heterocyclic aromatic or heterocyclic radical;

l, m and n are each independently an integer of from 1 to 5, and in addition n can be 0;

$Z_2$ is SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical; and May is a maytansinoid.

Such additional maytansines also include compounds represented by formula (VII):

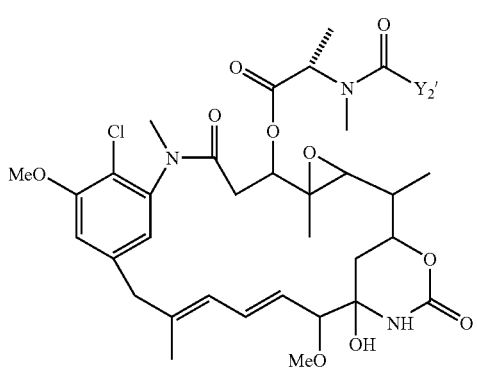
(VII)

wherein:
$Y_2'$ represents
$(CR_7R_8)_l(CR_9=CR_{10})_p(C\equiv C)_qA_o(CR_5R_6)_mD_u(CR_{11}=CR_{12})_r(C\equiv C)_sB_t(CR_3R_4)_nCR_1R_2SZ_2$,
wherein:

$R_1$ and $R_2$ are each independently linear branched or alkyl or alkenyl having from 1 to 10 carbon atoms, such as $CH_3$ and $C_2H_5$, cyclic alkyl or alkenyl having from 3 to 10 carbon atoms, phenyl, substituted phenyl or heterocyclic aromatic or heterocyclic radical, and in addition $R_2$ can be H;

A, B, and D each independently is cycloalkyl or cycloalkenyl having 3 to 10 carbon atoms, simple or substituted aryl, or heterocyclic aromatic or heterocyclic radical;

$R_3$, $R_4$, $R_5$, $R_6$, $R_7$, $R_8$, $R_9$, $R_{10}$, $R_{11}$, and $R_{12}$ are each independently H, linear alkyl or alkenyl having from 1 to 10 carbon atoms, such as $CH_3$ and $C_2H_5$, branched or cyclic alkyl or alkenyl having from 3 to 10 carbon atoms, phenyl, substituted phenyl or heterocyclic aromatic or heterocyclic radical;

l, m, n, o, p, q, r, s, t and u are each independently 0 or an integer of from 1 to 5, provided that at least two of l, m, n, o, p, q, r, s, t and u are not zero at any one time; and $Z_2$ is SR or —COR, wherein R is linear alkyl or alkenyl having from 1 to 10 carbon atoms, branched or cyclic alkyl or alkenyl having from 3-10 carbon atoms, or simple or substituted aryl or heterocyclic aromatic or heterocyclic radical.

Preferred embodiments of formula (VII) include compounds of formula (VII) wherein: $R_1$ is methyl and $R_2$ is H.

The above-mentioned maytansinoids can be conjugated to anti-CA6 antibody DS6, huN901, huC242, huCD33, MY9, trastuzumab, or a homologue or fragment thereof, wherein the antibody is linked to the maytansinoid using the thiol or disulfide functionality that is present on the acyl group of an acylated amino acid side chain found at C-3, C-14 hydroxymethyl, C-15 hydroxy or C-20 desmethyl of the maytansinoid, and wherein the acyl group of the acylated amino acid side chain has its thiol or disulfide functionality located at a carbon atom that has one or two substituents, said substituents being linear alkyl or alkenyl having from 1 to 10 carbon atoms, such as $CH_3$ and $C_2H_5$, branched or cyclic alkyl or alkenyl having from 3 to 10 carbon atoms, phenyl, substituted phenyl or heterocyclic aromatic or heterocyclic radical, and in addition one of the substituents can be H, and wherein the acyl group has a linear chain length of at least three carbon atoms between the carbonyl functionality and the sulfur atom.

A preferred conjugate of the present invention is the one that comprises the anti-anti-CA6 antibody DS6, huN901, huC242, huCD33, MY9, trastuzumab, or a homologue or fragment thereof or a homologue or fragment thereof, conjugated to a maytansinoid of formula (VIII):

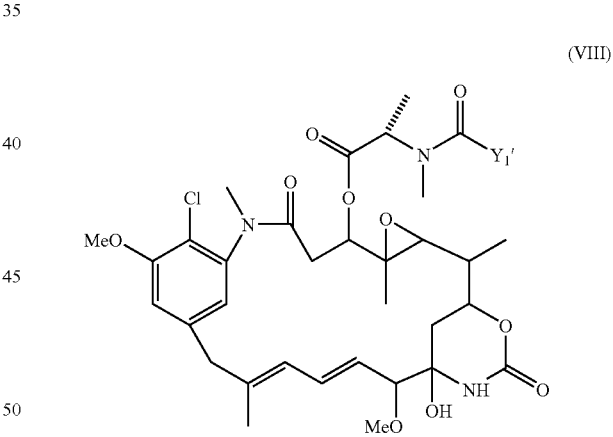
(VIII)

wherein:
$Y_1'$ represents
$(CR_7R_8)_l(CR_9=CR_{10})_p(C\equiv C)_qA_o(CR_5R_6)_mD_u(CR_{11}=CR_{12})_r(C\equiv C)_sB_t(CR_3R_4)_nCR_1R_2S$—,
wherein:

A, B, and D, each independently is cycloalkyl or cycloalkenyl having 3 to 10 carbon atoms, simple or substituted aryl, or heterocyclic aromatic or heterocyclic radical;

$R_3$, $R_4$, $R_5$, $R_6$, $R_7$, $R_8$, $R_9$, $R_{10}$, $R_{11}$, and $R_{12}$ are each independently H, linear alkyl or alkenyl having from 1 to 10 carbon atoms, such as $CH_3$ and $C_2H_5$, branched or cyclic alkyl or alkenyl having from 3 to 10 carbon atoms, phenyl, substituted phenyl or heterocyclic aromatic or heterocyclic radical; and l, m, n, o, p, q, r, s, t and u are each independently 0 or an integer of from 1 to 5, provided that at least two of l, m, n, o, p, q, r, s, t and u are non-not zero at any one time.

Preferably, $R_1$ is methyl and $R_2$ is H or $R_1$ and $R_2$ are methyl.

An even more preferred conjugate of the present invention is the one that comprises the anti-CA6 antibody DS6, huN901, huC242, huCD33, MY9, trastuzumab, or a homologue or fragment thereof or a homologue or fragment thereof, conjugated to a maytansinoid of formula (IX-L), (IX-D), or (IX-D,L):

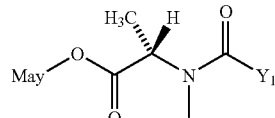

IX-L

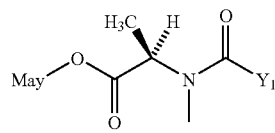

IX-D

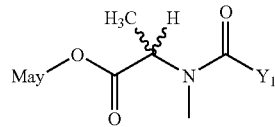

IX-D,L wherein:

$Y_1$ represents $(CR_7R_8)_l(CR_5R_6)_m(CR_3R_4)_nCR_1R_2S—$, wherein:

$R_1$ and $R_2$ are each independently linear alkyl or alkenyl having from 1 to 10 carbon atoms, such as $CH_3$ and $C_2H_5$, branched or cyclic alkyl or alkenyl having from 3 to 10 carbon atoms, phenyl, substituted phenyl, heterocyclic aromatic or heterocyclic radical, and in addition $R_2$ can be H;

$R_3$, $R_4$, $R_5$, $R_6$, $R_7$ and $R_8$ are each independently H, linear alkyl or alkenyl having from 1 to 10 carbon atoms, such as $CH_3$ and $C_2H_5$, branched or cyclic alkyl or alkenyl having from 3 to 10 carbon atoms, phenyl, substituted phenyl or heterocyclic aromatic or heterocyclic radical;

l, m and n are each independently an integer of from 1 to 5, and in addition n can be 0; and May represents a maytansinol which bears the side chain at C-3, C-14 hydroxymethyl, C-15 hydroxy or C-20 desmethyl.

Preferred embodiments of formulas (IX-L), (IX-D) and (IX-D,L) include compounds of formulas (IX-L), (IX-D) and (IX-D,L) wherein:

$R_1$ is methyl and $R_2$ is H or $R_1$ and $R_2$ are methyl, $R_1$ is methyl, $R_2$ is H, $R_5$, $R_6$, $R_7$ and $R_8$ are each H; l and m are each 1; n is 0, $R_1$ and $R_2$ are methyl; $R_5$, $R_6$, $R_7$ and $R_8$ are each H; l and m are 1; n is 0.

Preferably the cytotoxic agent is represented by formula (IX-L).

A further preferred conjugate of the present invention is the one that comprises the anti-CA6 antibody DS6, huN901, huC242, huCD33, MY9, trastuzumab, or a homologue or fragment thereof or a homologue or fragment thereof, conjugated to a maytansinoid of formula (X):

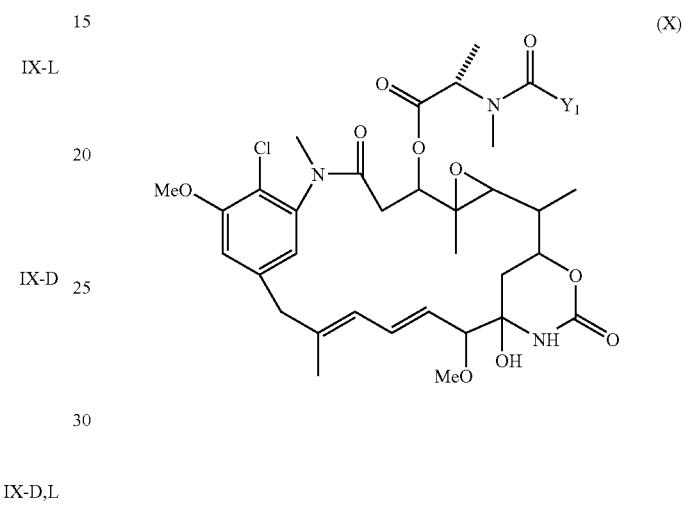

(X)

wherein the substituents are as defined for formula (IX) above.

Especially preferred are any of the above-described compounds, wherein $R_1$ is methyl, $R_2$ is H, $R_5$, $R_6$, $R_7$ and $R_8$ are each H, l and m are each 1, and n is 0.

Further especially preferred are any of the above-described compounds, wherein $R_1$ and $R_2$ are methyl, $R_5$, $R_6$, $R_7$, $R_8$ are each H, l and m are 1, and n is 0

Further, the L-aminoacyl stereoisomer is preferred.

Each of the maytansinoids taught in U.S. patent publication No. 2004/0235840, published Nov. 25, 2004 may also be used in the cytotoxic conjugate of the present invention. The entire disclosure of U.S. patent publication No. 2004/0235840, published Nov. 25, 2004 is incorporated herein by reference.

Disulfide-Containing Linking Groups

In order to link the maytansinoid to a cell binding agent, such as the DS6, huN901, huC242, huCD33, MY9, or trastuzumab antibody, the maytansinoid comprises a linking moiety. The linking moiety contains a chemical bond that allows for the release of fully active maytansinoids at a particular site. Suitable chemical bonds are well known in the art and include disulfide bonds, acid labile bonds, photolabile bonds, peptidase labile bonds and esterase labile bonds. Preferred are disulfide bonds.

The linking moiety also comprises a reactive chemical group. In a preferred embodiment, the reactive chemical group can be covalently bound to the maytansinoid via a disulfide bond linking moiety.

Particularly preferred reactive chemical groups are N-succinimidyl esters and N-sulfosuccinimidyl esters.

Particularly preferred maytansinoids comprising a linking moiety that contains a reactive chemical group are C-3 esters of maytansinol and its analogs where the linking moiety contains a disulfide bond and the chemical reactive group comprises a N-succinimidyl or N-sulfosuccinimidyl ester.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. However the C-3 position is preferred and the C-3 position of maytansinol is especially preferred.

The synthesis of maytansinoids and maytansinoid derivatives having a disulfide moiety that bears a reactive group is described in U.S. Pat. Nos. 6,441,163 and 6,333,410, and U.S. application Ser. No. 10/161,651, each of which is herein incorporated by reference.

The reactive group-containing maytansinoids, such as DM1, are reacted with an antibody, such as the DS6, huN901, huC242, huCD33, MY9, or trastuzumab antibody, to produce cytotoxic conjugates. These conjugates may be purified by HPLC or by gel-filtration.

Several excellent schemes for producing such antibody-maytansinoid conjugates are provided in U.S. Pat. Nos. 6,716,821, 6,441,163, and 6,333,410, and in U.S. patent publication no. 2003/0055226, published Mar. 20, 2003, each of which is incorporated herein in its entirety.

In general, a solution of an antibody in aqueous buffer may be incubated with a molar excess of maytansinoids having a disulfide moiety that bears a reactive group. The reaction mixture can be quenched by addition of excess amine (such as ethanolamine, taurine, etc.). The maytansinoid-antibody conjugate may then be purified by gel-filtration.

The number of maytansinoid molecules bound per antibody molecule can be determined by measuring spectrophotometrically the ratio of the absorbance at 252 nm and 280 nm. An average of 1-10 maytansinoid molecules/antibody molecule is preferred.

Conjugates of antibodies with maytansinoid drugs can be evaluated for their ability to suppress proliferation of various unwanted cell lines in vitro. For example, cell lines such as the human epidermoid carcinoma line A-431, the human small cell lung cancer cell line SW2, the human breast tumor line SKBR3 and the Burkitt's lymphoma line Namalwa can easily be used for the assessment of cytotoxicity of these compounds. Cells to be evaluated can be exposed to the compounds for 24 hours and the surviving fractions of cells measured in direct assays by known methods. $IC_{50}$ values can then be calculated from the results of the assays.

Taxanes

The cytotoxic agent used in the cytotoxic conjugates according to the present invention may also be a taxane or derivative thereof.

Taxanes are a family of compounds that includes paclitaxel (Taxol), a cytotoxic natural product, and docetaxel (Taxotere), a semi-synthetic derivative, two compounds that are widely used in the treatment of cancer. Taxanes are mitotic spindle poisons that inhibit the depolymerization of tubulin, resulting in cell death. While docetaxel and paclitaxel are useful agents in the treatment of cancer, their antitumor activity is limited because of their non-specific toxicity towards normal cells. Further, compounds like paclitaxel and docetaxel themselves are not sufficiently potent to be used in conjugates of cell binding agents.

A preferred taxane for use in the preparation of cytotoxic conjugates is the taxane of formula (XI):

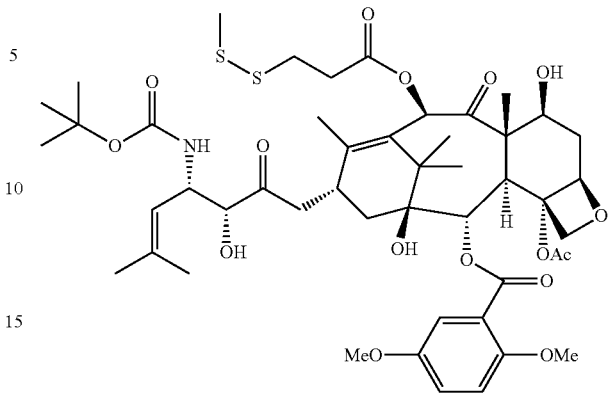

(XI)

Methods for synthesizing taxanes that may be used in the cytotoxic conjugates of the present invention, along with methods for conjugating the taxanes to cell binding agents such as antibodies, are described in detail in U.S. Pat. Nos. 5,416,064, 5,475,092, 6,340,701, 6,372,738, 6,436,931, 6,716,821, and 6,596,757 and in U.S. patent publication nos, 2003/0014048, published Jan. 16, 2003 and 2004/0024049, published Feb. 5, 2004.

CC-1065 Analogues

The cytotoxic agent used in the cytotoxic conjugates according to the present invention may also be CC-1065 or a derivative thereof.

CC-1065 is a potent anti-tumor antibiotic isolated from the culture broth of *Streptomyces zelensis*. CC-1065 is about 1000-fold more potent in vitro than are commonly used anti-cancer drugs, such as doxorubicin, methotrexate and vincristine (B. K. Bhuyan et al., *Cancer Res.*, 42, 3532-3537 (1982)). CC-1065 and its analogs are disclosed in U.S. Pat. Nos. 6,372,738, 6,340,701, 5,846,545 and 5,585,499.

The cytotoxic potency of CC-1065 has been correlated with its alkylating activity and its DNA-binding or DNA-intercalating activity. These two activities reside in separate parts of the molecule. Thus, the alkylating activity is contained in the cyclopropapyrroloindole (CPI) subunit and the DNA-binding activity resides in the two pyrroloindole subunits.

Although CC-1065 has certain attractive features as a cytotoxic agent, it has limitations in therapeutic use. Administration of CC-1065 to mice caused a delayed hepatotoxicity leading to mortality on day 50 after a single intravenous dose of 12.5 µg/kg {V. L. Reynolds et al., J. Antibiotics, XXIX, 319-334 (1986)}. This has spurred efforts to develop analogs that do not cause delayed toxicity, and the synthesis of simpler analogs modeled on CC-1065 has been described {M. A. Warpehoski et al., J. Med. Chem., 31, 590-603 (1988)}.

In another series of analogs, the CPI moiety was replaced by a cyclopropabenzindole (CBI) moiety {D. L. Boger et al., J. Org. Chem., 55, 5823-5833, (1990), D. L. Boger et al., BioOrg. Med. Chem. Lett., 1, 115-120 (1991)}. These compounds maintain the high in vitro potency of the parental drug, without causing delayed toxicity in mice. Like CC-1065, these compounds are alkylating agents that bind to the minor groove of DNA in a covalent manner to cause cell death. However, clinical evaluation of the most promising analogs, Adozelesin and Carzelesin, has led to disappointing results {B. F. Foster et al., Investigational New Drugs, 13, 321-326 (1996); I. Wolff et al., Clin. Cancer Res., 2, 1717-

1723 (1996)}. These drugs display poor therapeutic effects because of their high systemic toxicity.

The therapeutic efficacy of CC-1065 analogs can be greatly improved by changing the in vivo distribution through targeted delivery to the tumor site, resulting in lower toxicity to non-targeted tissues, and thus, lower systemic toxicity. In order to achieve this goal, conjugates of analogs and derivatives of CC-1065 with cell-binding agents that specifically target tumor cells have been described {U.S. Pat. Nos. 5,475,092; 5,585,499; 5,846,545}. These conjugates typically display high target-specific cytotoxicity in vitro, and exceptional anti-tumor activity in human tumor xenograft models in mice {R. V. J. Chari et al., Cancer Res., 55, 4079-4084 (1995)}.

Methods for synthesizing CC-1065 analogs that may be used in the cytotoxic conjugates of the present invention, along with methods for conjugating the analogs to cell binding agents such as antibodies, are described in detail in U.S. Pat. Nos. 5,475,092, 5,846,545, 5,585,499, 6,534,660, 6,586,618, and 6,756,397 and in U.S. patent publication no. 2003/0195365, published Oct. 16, 2003.

Other Drugs

Drugs such as methotrexate, daunorubicin, doxorubicin, vincristine, vinblastine, melphalan, mitomycin C, chlorambucil, calicheamicin, tubulysin and tubulysin analogs, duocarmycin and duocarmycin analogs, dolastatin and dolastatin analogs are also suitable for the preparation of conjugates of the present invention. The drug molecules can also be linked to the antibody molecules through an intermediary carrier molecule such as serum albumin. Doxarubicin and Daunorubicin compounds, as described, for example, in U.S. Pat. No. 6,630,579, may also be useful cytotoxic agents.

Compositions and Methods of Use

The present invention provides pharmaceutical compositions comprising an effective amount of any of the drug-cell-binding agents of the present invention, pharmaceutically acceptable a salt or solvate thereof, and a pharmaceutically acceptable carrier, diluent or excipient.

The present invention also provides methods of treatment comprising administering to a subject in need of treatment an effective amount of any of the conjugates described above.

Similarly, the present invention provides a method for inducing cell death in heterogeneous or mixed cell population comprising contacting target cells or tissue containing target cells with an effective amount of a cytotoxic agent comprising any of the drug-cell-binding agents (e.g., maytansinoid, taxanes or CC 1065-cell-binding agents) of the present invention, a salt or solvate thereof. The target cells are cells to which the cell-binding agent can bind because they express a unique antigen expressed by these cells. The cytotoxic drug is cleaved from the conjugate in the targeted cell to release the drug and kill cells that lack the antigen expressed in targeted cells.

It also provides for killing of a heterogeneous or a mixed cell population, wherein the ligand was initially expressed on a particular cell or a tissue and then shed into the medium. Here the shed ligand is the target for the cell binding agent and the drug kills heterogeneous or mixed population of tumor cells in the vicinity of the shed antigen.

If desired, other active agents, such as other anti-tumor agents, may be administered along with the conjugate.

Suitable pharmaceutically acceptable carriers, diluents, and excipients are well known and can be determined by those of ordinary skill in the art as the clinical situation warrants.

Examples of suitable carriers, diluents and/or excipients include: (1) Dulbecco's phosphate buffered saline, pH about 7.4, containing or not containing about 1 mg/ml to 25 mg/ml human serum albumin, (2) 0.9% saline (0.9% w/v NaCl), and (3) 5% (w/v) dextrose; and may also contain an antioxidant such as tryptamine and a stabilizing agent such as Tween 20. The method for inducing cell death in selected cell populations can be practiced in vitro and in vivo. Examples of in vitro use are shown in the Examples section of this specification.

For clinical in vivo use, the cytotoxic agent of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 1000 ml of normal saline to which 5 to 10 ml of human serum albumin can be added. Dosages will be 10 μg to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of inducing cell death in selected cell populations include malignancy of any type including, for example, cancer of the lung, breast, colon, prostate, kidney, pancreas, ovary or any kind of neoplastic growth which includes a heterogeneous or a mixed abnormal cell population.

All references cited herein and in the examples that follow are expressly incorporated by reference in their entireties.

EXAMPLES

The broad scope of this invention is best understood with reference to the following examples, which are not intended to limit the invention to specific embodiments.

Example 1

Bystander Effect of Antibody-Drug Conjugates

Materials and Methods

Immunoconjugates

Preparation of immunoconjugates: The maytansinoid DM1 ($N^{2'}$-deacetyl-$N^{2'}$-(3-mercapto-1-oxopropyl)-maytansine) was synthesized from the microbial fermentation product ansamitocin P-3 as described previously {Chari, R. V., et al., Cancer Res., 52, 127-31 (1992); U.S. Pat. No. 6,333,410}. The synthesis of the analogue of CC-1065, 5-[(3-mercapto-1-oxopropyl)amino]-bis-indolyl-(seco)-1,2,9,9a-tetrahydrocyclopropa[c]benz[e]indol-4-one, DC1, has been reported elsewhere {Chari, R. V., et al., Cancer Res. 55, 4079-84 (1995)}. The humanization of the C242 antibody (huC242) was done by the resurfacing method that has been described previously {Roguska M. A., et al., Proc Natl Acad Sci USA, 91, 969-73 (1994)}. Antibody-drug conjugates were prepared using N-succinimidyl-4-(2-pyridyldithio)pentanoate for disulfide linkage or N-succinimidyl-4-(N-maleimidomethyl)cyclohexane-1-carboxylate (SMCC) for thioether linkage as described elsewhere {Liu, C., et al., Proc Natl Acad Sci USA, 93, 8618-23 (1996); Chari, R. V., et al., Cancer Res., 52, 127-31 (1992)}. The immunoconjugates used in this study contained, on the average, 3.5 cytotoxic drug molecules, DM1 or DC1, per antibody molecule.

Cell Lines

COLO 205 (human colon adenocarcinoma, ATCC CCL-222), HL-60 (human acute promyelocytic leukemia, ATCC CCL-240) and Namalwa (human Burkitt's lymphoma, ATCC CRL-1432) cultures were maintained in RPMI-1640 medium supplemented with 10% heat-inactivated fetal bovine serum and 50 µg/mL gentamicin sulfate. HT-29 (human colon adenocarcinoma, ATCC HTB-38), A375 (human malignant melanoma, ATCC CRL-1619) and HepG2 (human hepatocellular carcinoma, ATCC HB-8065) cultures were maintained in DMEM medium supplemented with 10% heat-inactivated fetal bovine serum and 50 µg/mL gentamicin sulfate. SNU-16 (gastric carcinoma, ATCC CRL-5974) culture was maintained in modified RPMI-1640 medium (ATCC, 30-2003) supplemented with 10% heat-inactivated fetal bovine serum and 50 µg/mL gentamicin sulfate. All cell lines were cultured in a humidified incubator at 37° C., 6% $CO_2$.

Binding of the huC242 Antibody to CanAg

The binding of the huC242 antibody to CanAg-positive cells was evaluated by an indirect immunofluorescence assay utilizing flow cytometry. Cells ($5 \times 10^4$ per well) were plated in a round bottom 96-well plate and incubated at 4° C. for 3 h with serial dilutions of huC242 antibody in 0.2 mL of alpha-MEM medium supplemented with 2% (v/v) normal goat serum (Sigma). Each sample was assayed in triplicate. Control wells lacked huC242. The cells were then washed with 0.2 mL cold (4° C.) medium and stained with fluorescein-labeled goat anti-human IgG antibody for 1 h at 4° C. The cells were again washed with medium, fixed in 1% formaldehyde/PBS solution and analyzed using a FACSCalibur™ flow cytometer (BD Biosciences, San Jose, Calif.).

3D Collagen Cytotoxicity Assay

COLO 205 cells ($2 \times 10^5$ cells per mL) were treated with huC242-DM1 ($1 \times 10^{-8}$ M of conjugated antibody, 24 h incubation at 37° C., 6% $CO_2$), 1% formaldehyde (20 min incubation), or 5 Gy UV irradiation (UV Stratalinker 1800, Stratagene, Calif.). Treated cells were washed three times with 20-30 mL of fresh culture medium, and resuspended in culture medium at $1 \times 10^8$ cells per mL. Untreated COLO 205, Namalwa, A375 and HepG2 cells were washed and resuspended in a similar manner. One microliter of each of the untreated cell suspensions was then mixed with 0, 1, 2, 4, or 8 µL of the treated COLO 205 cells. One hundred microliters of ice-cold collagen gel solution (3D Collagen Cell Culture system, Chemicon International) was added to the cell mixtures, and the cell-collagen mixtures were dispensed immediately (5 µL per well) in round-bottom 96-well plates. The plates were incubated at 37° C. for 1 h to allow polymerization of the collagen. Fresh culture medium (200 µL) was then gently added to each well. Five to six days later, the number of viable cells was determined using a calorimetric cell proliferation assay measuring the reduction of MTT tetrasolium salt (1-(4,5-dimethylthiazol-2-yl)-3,5-diphenylformazan, Sigma) to formazan by live cells. Fifty microliters of the MTT stock solution (5 mg/mL in phosphate buffered saline) was added to each well. The plates were incubated at 37° C. for 3 h and then centrifuged for 10 min at 860×g. Culture medium was aspirated from each well, the formazan crystals were solubilized with dimethyl sulfoxide (100 µL per well) and $OD_{540nm}$ was measured. The relative number of cells (cell survival) in each well was calculated by correcting for the medium background reading, and then dividing each value by the average of the values in the control (untreated cells) wells.

Liquid Culture Cytotoxicity Assay

Dilutions of immunoconjugates in the appropriate medium were added to wells of 96-well round-bottom plates containing either $2 \times 10^3$ COLO 205 cells, or $2 \times 10^3$ SNU-16 cells, or $2 \times 10^3$ Namalwa cells, or a mixture of $2 \times 10^3$ COLO 205 with $2 \times 10^3$ Namalwa cells, or a mixture of $2 \times 10^3$ SNU-16 with $2 \times 10^3$ Namalwa cells. The plates were incubated for five days at 37° C., 6% $CO_2$. Pictures of the cells in each well were then taken with a Nikon Diaphot 300 inverted microscope.

ELISA Assays for the Quantitation of huC242-DM1, huC242-SMCC-DM1, and Maytansinoid Drug Released from the Conjugate The methods have been described previously {Xie, H., et al., J Pharmacol Exp Ther, 308, 1073-82 (2004)}. Briefly, to measure the concentrations of huC242-DM1, the conjugate from either the standard, or the test samples was captured on ELISA plates coated with a murine anti-maytansinoid monoclonal antibody (ImmunoGen), and detected with horseradish peroxidase-labeled donkey anti-human IgG (Jackson ImmunoResearch, West Grove, Pa.). To determine the concentration of the maytansinoid drug released from the conjugate, protein was precipitated from samples by addition of five volumes of ice-cold acetone. Precipitated protein was sedimented by centrifugation at 16,000×g, and the concentrations of released drug in the supernatant were determined using a competition ELISA as follows. Plates were coated with DM1 that had been conjugated to bovine serum albumin (BSA-DM1, ImmunoGen). Dilution samples of a maytansine standard solution and test samples were mixed with biotinylated murine anti-maytansinoid monoclonal antibody (ImmunoGen) and then incubated in the BSA-DM1-coated plate. Finally, the bound biotinylated anti-maytansinoid antibody was detected with streptavidin-horseradish peroxidase (Jackson ImmunoResearch).

Human Xenograft Tumor Models in Mice

Five-week-old female CB-17 severe combined immunodeficient (SCID) mice were obtained from Taconic (Germantown, N.Y.). One week later, mice were inoculated subcutaneously with one of the following cell lines: HT-29 ($2 \times 10^6$ cells per mouse), COLO 205 ($1 \times 10^7$), Namalwa ($2 \times 10^6$), or a mixture of COLO 205 and Namalwa cells ($1 \times 10^7$ and $2 \times 10^6$ cells per mouse, respectively). Nine to thirteen days later, each mouse received daily intravenous bolus injections of PBS (control), huC242-SMCC-DM1, or huC242-DM1 containing 25, 75, or 150 µg/kg of conjugated DM1 on five consecutive days (qd×5). Tumor dimensions were measured twice per week and the volume was calculated as ½(L×W×H) where L is the length, W the width, and H the height of the tumor.

Immunohistochemistry

Tumor tissues were fixed in 10% formalin and embedded in paraffin. Immunohistochemical examination of the paraffin sections was performed using murine C242 antibody to detect COLO 205 cells, and murine anti-CD38 antibody (RDI-CD38abm-290, Research Diagnostic, Flanders, N.J.) to detect Namalwa cells using the avidin-biotin-peroxidase (ABC) technique.

Results:

HuC242-DM1 Kills Non-Target Cells Proximal to its Target Cells In Vitro

The immunoconjugate, cantuzumab mertansine or huC242-DM1, is effective in eradicating CanAg-expressing human tumor xenografts in mice, including those that express the antigen in a heterogeneous manner, {Liu, C., et al., Proc Natl Acad Sci USA, 93, 8618-23 (1996)} but is not effective against CanAg negative xenograft tumors. To determine if the huC242-DM1 conjugate associated with the CanAg-positive cells has the ability to kill neighboring non-targeted cells, its behavior was studied in vitro using antigen-positive and antigen-negative mixed cell cultures in a 3D collagen matrix.

Cells can be embedded into the matrix at high densities simulating the in vivo tumor environment.

In a first series of experiments, treated and untreated antigen-positive COLO 205 cells (FIG. 2) were used. One set of cells was incubated in culture medium with huC242-DM1 at 37° C. for 16 h. The unbound conjugate was then removed by extensive washing, and increasing numbers of treated cells were mixed with samples of untreated cells to give ratios of treated to untreated cells of 0:1 (control), 1:1, 4:1, and 8:1, respectively. The cell mixtures were then embedded into collagen, incubated for five days, and the number of viable cells in each sample was determined in an MTT assay. In further control cultures, the immunoconjugate-treated COLO 205 cells were replaced by formaldehyde-treated or UV-light-treated COLO 205 cells. The results are shown in FIG. 3A. The surviving fraction of cells progressively decreased in the cultures containing increasing numbers of conjugate-treated cells (FIG. 3A, black bars). Thus untreated cells were killed in the mixed cultures. This killing was conjugate-dependent and not due to any inhibitory effect of dying COLO 205 cells on the untreated cell population, since COLO 205 cells killed by either formaldehyde treatment or UV irradiation did not significantly affect the proliferation of the untreated cells (FIG. 3A, grey and white bars, respectively).

Figure 3A:
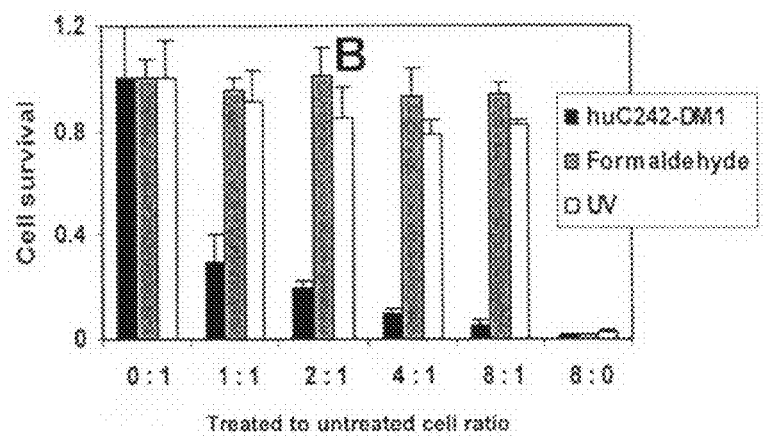
FIG. 3. Histograms showing that immunoconjugates linked via a disulfide, but not thioether, bond kill non-target cells located proximally to its target cells in vitro.
Figure 3B:
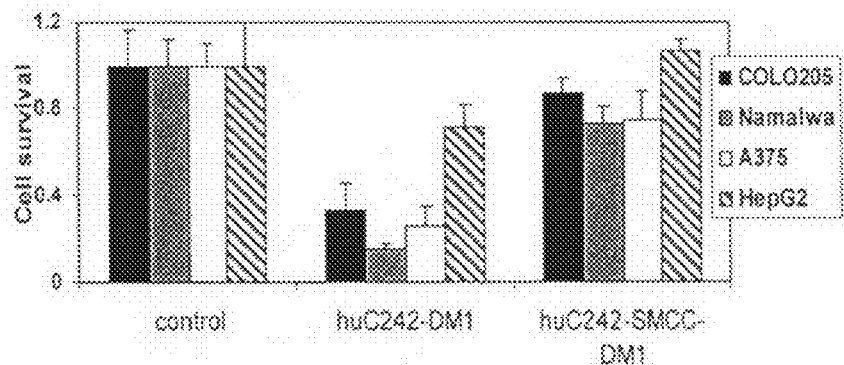

In a second series of experiments, COLO-205 cells treated with huC242-DM1, as described above, were mixed with antigen-negative cell lines at a ratio of 1:1, embedded in collagen, incubated for five days, and then assayed for cell growth in an MTT assay. The antigen-negative cell lines were of diverse origins: a Burkitt's lymphoma (Namalwa), a melanoma (A375), and a hepatocarcinoma (HepG2). As shown in FIG. 3B, huC242-DM1-treated cells inhibited the growth of all co-cultured, antigen-negative cell lines. Namalwa cells were the most sensitive to the cytotoxic effect generated by conjugate pre-treated COLO 205 cells, as indicated by a decrease in the surviving fraction to less than 0.2, HepG2 cells were the least sensitive with a surviving fraction of about 0.7, and A375 and COLO 205 cells showed intermediate sensitivity.

Figure 3C:
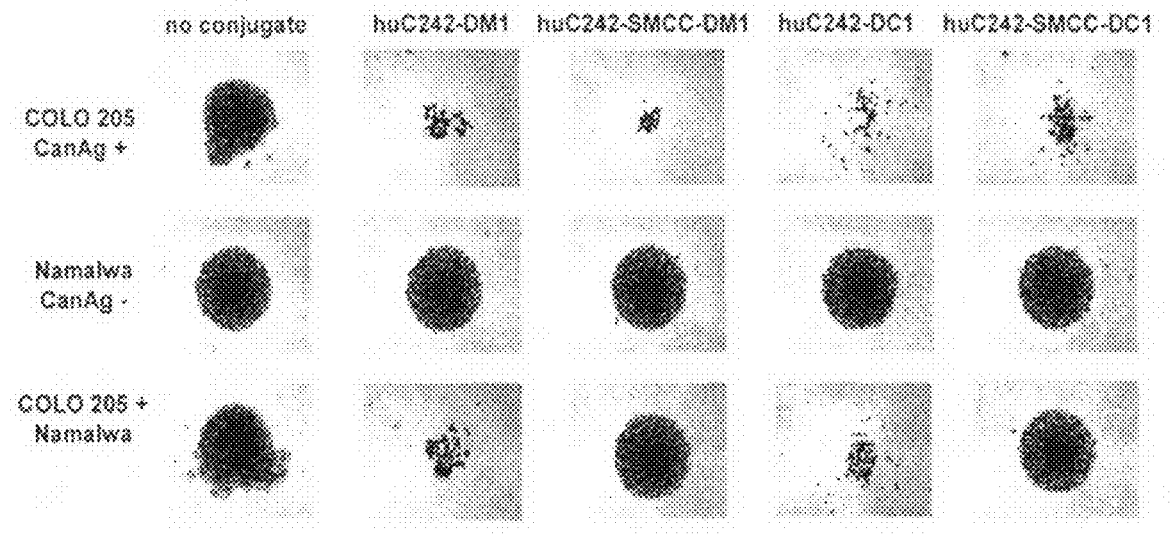

Whether the target cell-dependent killing of non-target cells also occurs in liquid cell cultures was examined next. Antigen-negative, non-adherent Namalwa cells were used as reporter cells in mixed cultures and semi-adherent COLO 205 as target cells. The two cell types were plated together in a 96-well round-bottom plate. Within a few hours all cells settled together in close proximity in the middle of the well. The experiment included wells that contained $2\times10^3$ Namalwa cells alone, $2\times10^3$ COLO 205 cells alone, and a mixture of $2\times10^3$ cells of each of the two cell lines, all in 0.2 mL liquid culture medium containing 1 nM huC242-DM1. After incubation for five days at 37° C., photographs were taken of the cell populations (FIG. 3C). In the absence of the conjugate (FIG. 3C, left column), the number of cells in all wells had increased some 20-fold as determined by cell counting. The mixed cell populations were also analyzed by flow cytometry to confirm that both the Namalwa and COLO 205 cells had proliferated. Alexa-labeled huC242 served to stain CanAg-positive COLO 205 cells, while the B cell-specific Alexa-labeled anti-CD19 antibody was used for detection of the Namalwa cells. This analysis revealed that after five days of proliferation, conjugate-free mixed cultures consisted of 40% COLO 205 cells and 60% Namalwa cells, demonstrating that both cell types had proliferated at similar rates. As expected, huC242-DM1 killed most cells in wells containing CanAg-positive COLO 205 cells (FIG. 3C, top row) and did not significantly affect the growth in wells containing antigen-negative Namalwa cells (FIG. 3C, middle row). In wells with a mixed population of cells, the conjugate killed both COLO 205 and Namalwa cells (FIG. 3C, bottom row). Thus, huC242-DM1-treated COLO 205 cells can eradicate proximal antigen-negative cells in liquid culture as well as in a 3D collagen cell culture.

Figure 2:
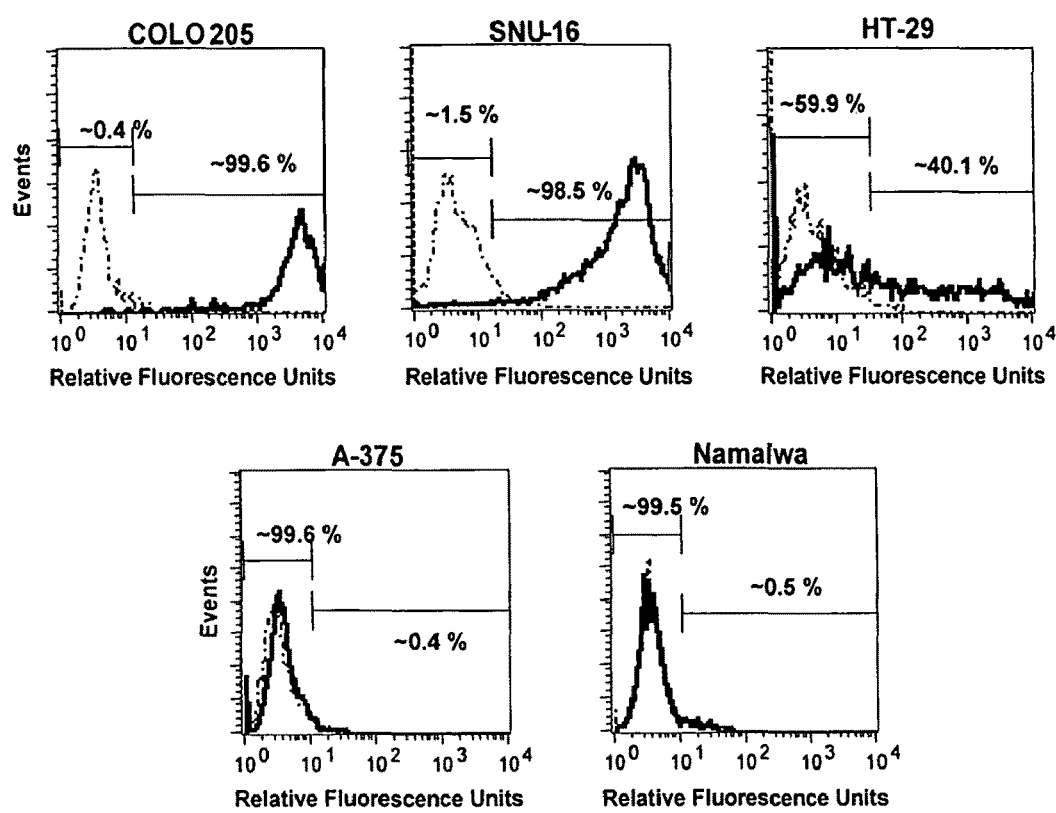
FIG. 2. Histograms of huC242 antibody binding to colon adenocarcinoma cell lines COLO 205 and HT-29, the gastric carcinoma cell line SNU-16, the melanoma cell line A375, and the Burkitt's lymphoma cell line Namalwa. The cells were incubated with huC242 and then stained with fluorescence-labeled anti-human IgG as described in *Materials and Methods*, Example 1. The cell associated fluorescence was measured on a fluorescence-activated cell sorter (FACS) and the histograms are shown in solid lines. Dashed lines represent the histograms of cells stained with fluorescence-labeled anti-human IgG without pre-incubation with huC242 (background staining). The percentages of antigen-positive and the antigen-negative cells are given in numbers.
Figure 3D:
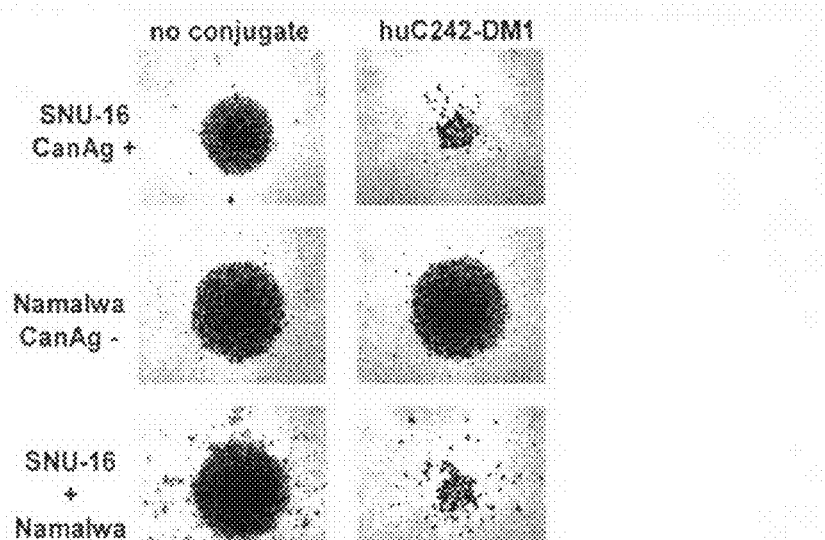

To test if target cell lines other than COLO 205 can exert this cytotoxic effect onto bystander cells, an analogous experiment was performed using another CanAg-positive cell line, the gastric carcinoma SNU-16 (FIG. 2). As shown in FIG. 3D, huC242-DM1 (1 nM) killed SNU-16 cells, did not affect the proliferation of Namalwa cells, and killed the mixed Namalwa/SNU-16 cell population. Together, these experiments demonstrate that the in vitro bystander effect of huC242-DM1 is not limited either to a particular type of CanAg-positive target cell or a particular type of CanAg-negative bystander cell.

Bystander Effect of Immunoconjugates is Affected by the Nature of the Antibody-Drug Linker HuC242-DM1 consists of DM1 molecules conjugated to the huC242 antibody through a disulfide-containing linker. This linker is readily reduced by thiols in vitro in a cell-free environment, and therefore is likely to be cleavable by abundant cell-associated thiols. To test whether the presence of the disulfide bond in the linker is required for generation of the bystander effect, huC242-SMCC-DM1, a conjugate in which DM1 is linked to the antibody via a non-reducible thioether bond (FIG. 1) was synthesized, and its in vitro cytotoxicity was tested on COLO 205 cells, Namalwa cells, and mixed COLO 205/Namalwa cell populations. huC242-SMCC-DM1 was as potent as huC242-DM1 in killing COLO 205 target cells with an $IC_{50}$ value of $4\times10^{-11}$ M (data not shown). This cytotoxicity was CanAg-selective since neither of the conjugates was cytotoxic for the antigen-negative Namalwa cells in the entire concentration range tested (up to $1\times10^{-9}$ M). Unlike huC242-DM1, huC242-SMCC-DM1 displayed only marginal, if any, cytotoxicity on bystander cells in either the 3D collagen matrix assay, or liquid culture assay (FIGS. 3B and 3C, respectively), suggesting that the mechanism of the bystander effect for huC242-DM1 includes a disulfide bond cleavage step.

Bystander Effect is not Limited to Antibody-Maytansinoid Conjugates

To determine if the bystander effect is a unique property of antibody-maytansinoid conjugates, conjugates of huC242 with DC1 were examined. DC1 is an analog of the minor grove-binding DNA alkylator CC-1065 and differs from DM1 in both its structure (FIG. 1) and mechanism of action. Previously potent antigen-selective conjugates of DC1 with an anti-CD19 antibody, and an anti-CD56 antibody was reported {Chari, R. V., et al., Cancer Res. 55, 4079-84 (1995)}. Analogous conjugates were constructed of DC 1 with huC242, in which the drug and the antibody were conjugated via either a disulfide-containing linker (huC242-DC1) or a thioether-containing linker (huC242-SMCC-DC1) as shown in FIG. 1, and their ability to kill antigen-positive and bystander cells in vitro was tested. At concentrations between $2\times10^{-10}$ M and $2\times10^{-9}$ M, either conjugate killed most of the cells in antigen-positive COLO 205 cultures (FIG. 3C, top row shows the results for the $1\times10^{-9}$ M concentration), but not the cells in antigen-negative Namalwa cultures (FIG. 3C, middle row), confirming that their cytotoxicity is antigen-dependent. When tested on mixed target/non-target cell populations, huC242-DC1 was able to kill most cells of both kinds, while huC242-SMCC-DC1 was not (FIG. 3C, bottom row). These experiments demonstrate that the ability to kill bystander cells is not an exclusive property of DM1- conjugates, but applies to other antibody-drug conjugates linked by disulfide-containing bonds.

Bystander Effect of huC242-DM1 is Generated Through Processing of the Conjugate by Target Cells and Release of a Cytotoxic Maytansinoid into the Medium To define the mechanism of the bystander effect, it was determined whether CanAg-expressing cells treated with huC242-DM1 release a cytotoxic compound into the medium, which then diffuses to neighboring cells. Target COLO 205 or antigen-negative Namalwa cells were incubated with huC242-DM1 or huC242-SMCC-DM1 ($10^{-7}$ M) at 37° C. for 0, 6, 24, or 48 h. The cells were removed from the medium by centrifugation, and the supernatants were assayed for the presence of huC242-DM1 and free maytansinoids using two different ELISA methods (see Materials and Methods). The results are shown in FIG. 4A-C. After a 48 h incubation with the target cells, the concentration of either conjugate in the supernatant decreased approximately 3-fold and, concomitantly, the concentration of a free maytansinoid species increased about 4-fold (FIG. 4A, C). A similar incubation of huC242-DM1 with CanAg-negative Namalwa cells did not lead to either disappearance of conjugate or appearance of a free maytansinoid in the medium (FIG. 4B), indicating that binding to the cell surface antigen is necessary for the processing of these conjugates and release of maytansinoid drugs into the medium.

Figure 4D:
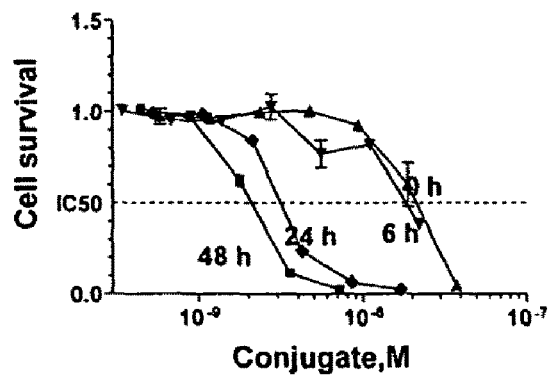
Figure 4E:
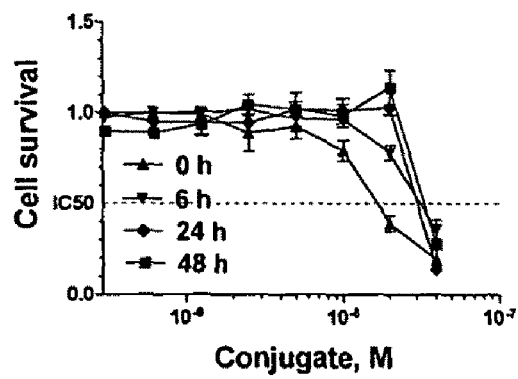

The cytotoxic activity of the released maytansinoid drugs was then assayed by exposing CanAg-negative Namalwa cells to the conjugate containing medium conditioned with COLO 205 cells. The non-specific cytotoxicity of huC242-DM1-containing medium gradually increased about 10-fold over 48 hours, as demonstrated by the change from an initial $IC_{50}$ value of $2 \times 10^{-8}$ M (supernatant harvested immediately after mixing, without incubation) to $3 \times 10^{-9}$ M and $1.7 \times 10^{-9}$ M after incubation for 24 h and 48 h, respectively (FIG. 4D). In contrast, no detectable increase in the cytotoxicity of huC242-DM1-containing medium occurred when it was conditioned by the presence of Namalwa cells (FIG. 4E). The enhanced cytotoxicity of conjugate-containing, COLO 205-conditioned medium parallels the increase in the concentration of the free maytansinoid in FIG. 4A. These data suggest a mechanism for the bystander cytotoxicity of huC242-DM1 in which the conjugate binds to antigen-expressing cells, followed by cell-mediated processing of the conjugate and progressive release of a cytotoxic maytansinoid species capable of killing neighboring cells.

Figure 4F:
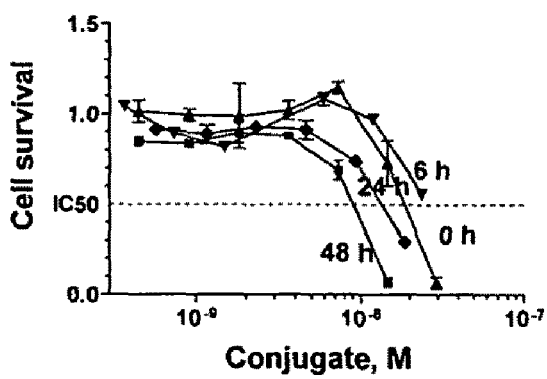

Incubation of huC242-SMCC-DM1 with COLO 205 cells led to only a modest 2-fold increase in non-specific cytotoxicity of the culture medium (FIG. 4F). Since both the disulfide-linked conjugate and the thioether linked conjugate are processed by COLO 205 cells and release a comparable amount of free maytansinoid species into the medium (FIGS. 4A and 4C), distinct mabolites are likely formed from huC242-DM1 and huC242-SMCC-DM 1. As described below, the chemical structures of the metabolites have been identified, and it has been confirmed that some of the products of the huC242-DM1 processing are 100 to 10,000 fold more potent than the metabolite of huC242-SMCC-SM1.

Bystander Effect of huC242-DM1 in Human Xenograft Tumor Models

Figure 5A:
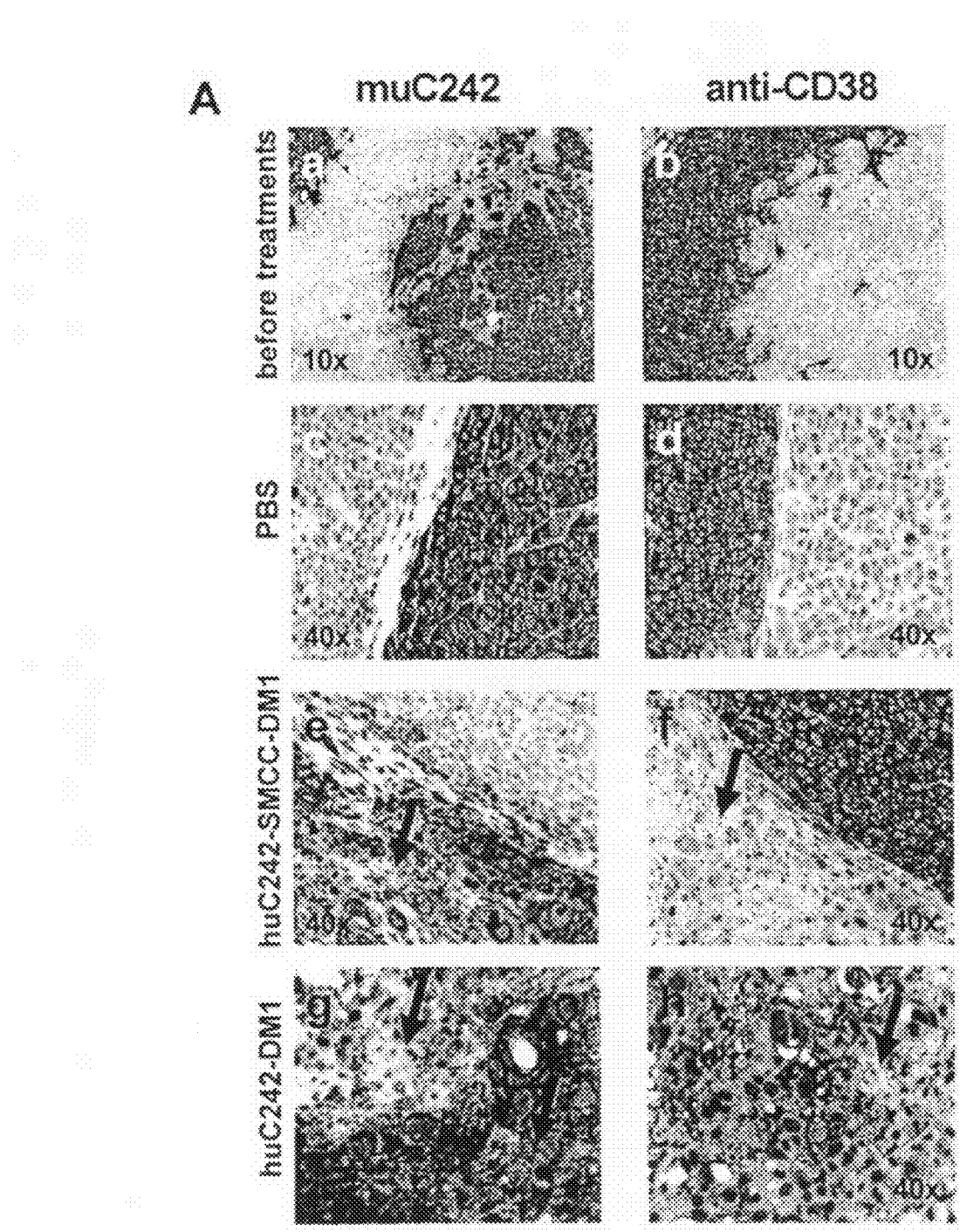
Figure 5B:
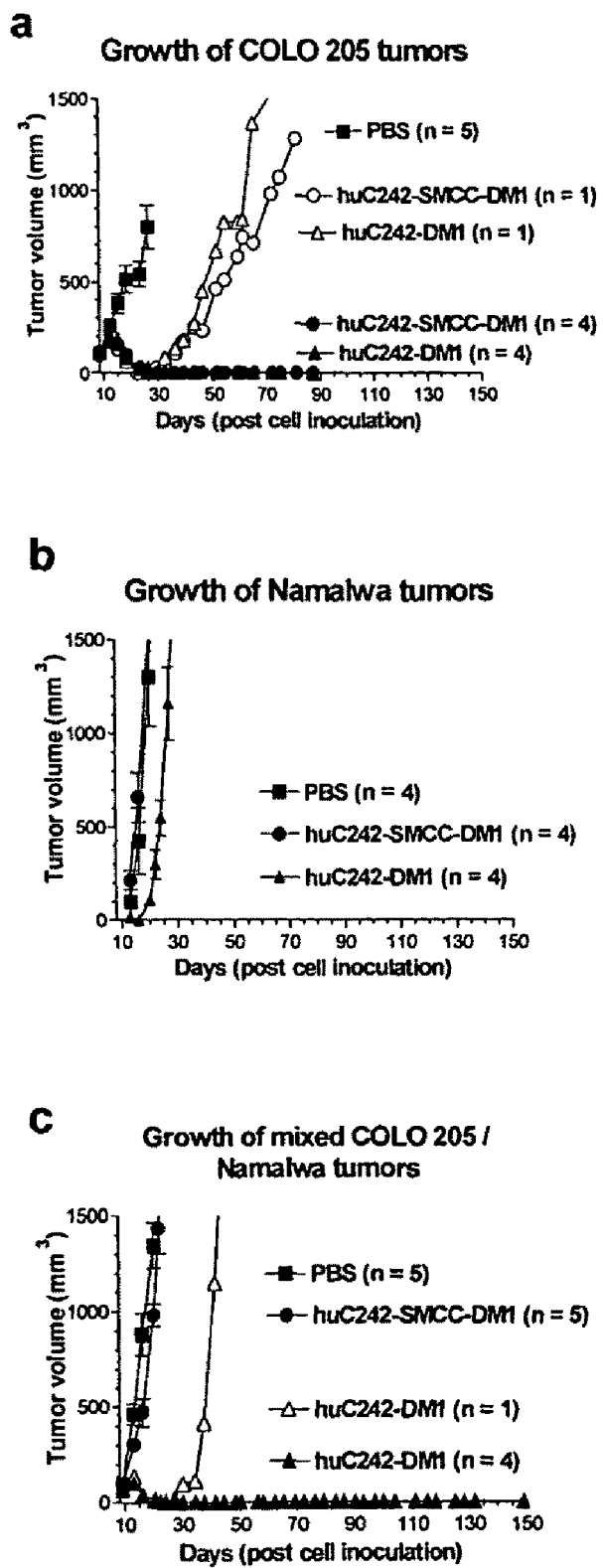

By analogy with the in vitro mixed cell culture systems, mixed xenograft tumor models were developed consisting of CanAg-expressing COLO 205 cells and CanAg-negative Namalwa cells. A mixture of COLO 205 and Namalwa cells was injected subcutaneously into SCID mice (a total of $1.2 \times 10^7$ cells/mouse). Every animal (a total of 23 mice) developed a measurable tumor and, nine days after the cell implanting, the mean tumor volume reached approximately 100 mm³. Two nine day-old tumors were removed from sacrificed animals and analyzed for the presence of COLO 205 cells (CanAg+/CD38−) and Namalwa cells (CD38+/CanAg−) by immunohistochemical staining of the tissues with the murine C242 antibody and a murine anti-CD38 antibody, respectively. The marker for COLO 205 cells (FIG. 5Aa) and that for Namalwa cells (FIG. 5Ab) stained areas of approximately equal size, confirming the mixed nature of the tumors. The vast majority of both COLO 205 cells and Namalwa cells appeared viable, with little necrosis apparent. Groups of mice bearing such mixed tumors of about 100 mm³ in size were then treated with five intravenous injections, given on five consecutive days (qd×5), of PBS (control group), huC242-SMCC-DM1, or huC242-DM1, at daily doses of the conjugates containing 150 μg/kg of linked DM1. One day after the last injection, two mice from each group were sacrificed and their tumors were analyzed by immunohistochemistry, as described above. In the PBS-treated control group, the tumor sections looked similar to those obtained from untreated tumors (compare FIGS. 5Ac with 5Aa, and 5Ad with 5Ab), with similarly sized areas of COLO 205 and Namalwa tissues, both displaying only a minimal degree of necrosis. Sections from tumors treated with huC242-SMCC-DM1 showed strongly necrotic COLO 205 tissue (50 to 60% necrotic, FIG. 5Ae) and healthy Namalwa tissue (FIG. 5Af). Finally, sections from tumors treated with huC242-DM1 showed a high degree of necrosis (70-80%) in both COLO 205 and Namalwa tissues (FIGS. 5Ag and 5Ah). These in vivo data mirror the in vitro results using mixed cell populations. The activity of the conjugate with the non-disulfide linker was restricted to the cells that express the target antigen, while the conjugate with the disulfide-containing linker killed both the target and the non-target tumor cells in the same tumor.

These immunohistochemistry results were in agreement with the effects of huC242-DM1 and huC242-SMCC-DM1 on the tumor growth. Treatment with either conjugate was equally effective against CanAg-positive COLO 205 tumors (FIG. 5Ba): tumors in four out of five mice completely regressed and did not relapse until day 90, when the experiment was terminated, and in each group, one mouse relapsed leading to a 28-day delay in the tumor growth. Neither conjugate was active on non-target Namalwa tumors: huC242-SMCC-DM1 treatment did not delay tumor growth while huC242-DM1 effected only a modest 7-day delay in tumor growth (FIG. 5Bb), confirming that the anti-tumor activities are CanAg-selective. The two conjugates differed markedly in their anti-tumor activity against mixed COLO 205-Namalwa tumors. huC242-SMCC-DM 1 did not delay the progression of mixed tumors, whereas huC242-DM1 caused complete regressions of tumors within two weeks (FIG. 5Bc) with four out of five mice remaining tumor-free until the end of the study (150 days, i.e. about 34 tumor doubling times). Immunohistochemical analysis of the only relapsed tumor in this group revealed that the tumor consisted entirely of Namalwa cells (data not shown). In conclusion, only the conjugate with the disulfide linker demonstrated an ability to kill bystander cells in vivo.

The in vivo bystander effect of huC242-DM1 and huC242-SMCC-DM1 in the HT-29 human colon cancer xenograft model in SCID mice was also assessed. HT-29 tumors are examples of special cases of "mixed" tumors that are generated spontaneously from a single cell line yet are heterogeneous with respect to antigen expression. HT-29 cells express the huC242 antibody target, CanAg, only on a minority of cells (20-40%) in vitro (FIG. 2) or in xenograft tumors {Liu, C, et al., Proc Natl Acad Sci USA; 93, 8618-23 (1996)}. Mice bearing established (about 130 mm$^3$) HT-29 tumors were treated with either huC242-DM1 or huC242-SMCC-DM1 at various doses (25 μg/kg, 75 μg/kg, or 100 μg/kg of linked DM1, qd×5), and tumor growth was monitored. Whereas the disulfide-linked conjugate huC242-DM1 induced marked tumor growth delays at each dose (5-25 days depending on the dose, FIG. 6A), the huC242-SMCC-DM1 conjugate produced only marginal anti-tumor effects (2.5-3.5 days of growth delay, FIG. 6B). Taken together, these data provide evidence that huC242-SMCC-DM1 conjugate containing a non-disulfide linker is efficacious only against tumors in which all proliferating cells express the target antigen. In contrast, the bystander effect associated with the disulfide-containing conjugate render this conjugate also effective against tumors in which only a fraction of cells expresses the CanAg target.

Example 2

Intracellular Activation of Antibody-Maytansinoid Conjugates

Abbreviations
BafA1, Bafilomycin A1
BSA, bovine serum albumin
FACS, fluorescence-activated cell sorter
HPLC, high pressure liquid chromatography
MTT, 1-(4,5-dimethylthiazol-2-yl)-3,5-diphenylformazan
NEM, N-ethylmaleimide
SPDB, N-succinimidyl 4-(2-pyridyldithio)butyrate
SMCC, N-succinimidyl 4-(N-maleimidomethyl)cyclohexane-1-carboxylate
DM1, $N^{2'}$-deacetyl-$N^{2'}$-(3-mercapto-1-oxopropyl)-maytansine
DM4, $N^{2'}$-deacetyl-$N^{2'}$-(4-mercapto-4-methyl-1-oxopentyl)-maytansine
DM1-SMe, $N^{2'}$-deacetyl-$N^{2'}$-[(3-methyldithio)-1-oxopropyl]-maytansine
DTT, dithiothreitol Materials and Methods RPMI 1640 and glutamine were from Cambrex Bioscience. Ultima Flo™ M scintillation fluid was from PerkinElmer life and analytical sciences. Gentamicin sulfate was from Gibco BRL. N-ethylmaleimide (NEM) and all other chemicals were obtained from Sigma. All antibodies used, huC242, Tras, and huB4 are humanized IgG1 antibodies. The maytansinoids [$^3$H]DM4, D-[$^3$H]DM4, S-methyl-DM4, lysine-$N^\epsilon$-SMCC-DM1, and lysine-$N^\epsilon$-SPDB-DM4, and the conjugates, huC242-SPDB-[$^3$H]DM4, huC242-SMCC-[$^3$H]DM4, Tras-SMCC-[$^3$H]DM4, and huB4-SPDB-[$^3$H]DM4, were prepared following published procedures {Chari, R. V., et al., Cancer Res, 52, 127-131 (1992) and Xie, H., et al., J Pharmacology and Experimental Therapeutics, 308, 1073-1082 (2004)}.

Treatment of COLO 205 Cells with Antibody-Drug Conjugates

COLO 205 cells (6×10$^6$) suspended in 3 mL culture medium containing an antibody-drug conjugate at a concentration of 10$^{-7}$M of conjugated antibody were incubated at 37° C. for 3-30 h. The cells and the medium were then separated by centrifugation (2000×g, 5 min). The supernatant (3 mL) was chilled on ice, mixed with 4 mL ice-cold acetone, and kept at −80° C. for at least 1 h or until further processing. The cells were suspended in 3 mL HBBS buffer and sedimented by centrifugation, then resuspended in 0.3 mL TBS containing 0.5% BSA. At this point, if alkylation was desired for capping of free thiols, NEM was added to 7.5 mM, the solution mixed, and kept at room temperature for 30 min. The cell suspension was then mixed with 0.6 mL ice cold acetone. The samples were placed at −80° C. for at least 1 h or until further processing. Media samples treated with acetone were removed from −80° C. Precipitated protein was removed by centrifugation at 2500×g and the supernatants were acidified with 5% acetic acid and evaporated to dryness. The samples were dissolved in 12 mL 20% aqueous CH$_3$CN containing 0.025% TFA, aliquots of 0.1 mL were submitted to HPLC.

In Vivo Studies

The anti-tumor activity of the conjugates was assessed in Female CB-17 SCID mice (Taconic Labs, Germantown, N.Y.) bearing HT-29 tumor as described previously {Liu, C., et al. Proc Natl Acad Sci USA, 93, 8618-23 (1996)}. Conjugates were administered intravenously to groups of 6 mice.

Cell Cycle Studies

Exponentially growing COLO 205 cells were resuspended at 1-2×10$^5$ cells/mL before drug or conjugate treatment. The nuclei of the cells were stained with propidium iodide as previously described {Firpo, E. J., et al., Mol Cell Biol, 14, 4889-901 (1994)}. DNA content analysis was performed using FACSCalibur (Becton Dickinson, San Jose, Calif.). 10,000 events per sample were collected, and FL2-A histograms generated for each sample. The cell cycle analysis software, ModFit LT 3.1 (Verity Software House, Topsham, Me.) was used to determine the percentage of cells in different phases of the cell cycle.

Analytical Methods

All maytansinoids were separated on an analytical C-18 column (0.46×25 cm) equilibrated with 20% aqueous CH$_3$CN containing 0.025% trifluoroacetic acid (TFA) and developed with a linear gradient of 2% CH$_3$CN min$^{-1}$ and a flow rate of 1 mL min$^{-1}$. The effluent was directed to a diode array detector followed either by a Radiomatic 150 β-counter (Perkin Elmer) where the effluent was mixed continuously with 3 mL of scintillation cocktail before it was directed to a 0.5 mL flow cell or a Bruker Daltonics Esquire 3000 electrospray mass spectrometer depending on the application. The data sampling interval was 6 s. The peak areas of the chromatograms were converted to picomoles as follows: A standard curve to relate the peak of radioactivity (mV$^2$) on the chromatograms to counts per minute (cpm) of tritium was prepared by injecting 1000 cpm to 50,000 cpm of a stock solution of [$^3$H]DM4 (250 mCi/mmol) diluted in 20% aqueous CH$_3$CN containing 0.025% TFA. Duplicates for each sample were submitted to HPLC as described above.

Results

In Vitro Potency and In Vivo Activity of huC242-Maytansinoid Conjugates

The disulfide-linked antibody-maytansinoid conjugate, huC242-SPDB-DM4, and the thioether-linked conjugate, huC242-SMCC-DM1, were first assayed for their cytotoxic potency against antigen-positive COLO 205 cells and antigen-negative Namalwa cells (both sensitive to maytansine with IC$_{50}$ values of about 30-60 pM for both cell lines) using an MTT-based assay. The conjugates displayed similar potencies with IC$_{50}$ values of 40 pM against COLO 205 cells and 20-80 nM against Namalwa cells upon a 4-day exposure of the cells to the conjugates (FIG. 7A). The anti-tumor activity of the two conjugates was assessed in SCID mice bearing subcutaneous HT-29 or COLO 205 tumors (both CanAg-positive human colon adenocarcinoma). The activity of huC242-SPDB-DM4 at a single dose of 50 μg/kg (concentration based on conjugated DM4) in eradicating HT-29 tumors was greater than that of huC242-SMCC-DM1 when administered as five daily injections at a dose of 150 µg/kg/day (FIG. 7B). HuC242-SPDB-DM4 also displayed greater activity than huC242-SMCC-DM1 when both were administered as five daily injections at a dose of 150 µg/kg/day in SCID mice bearing COLO 205 tumors (five out of five tumor free mice at 122 days as compared to two out of five tumor free mice at 122 days—data not shown). These results demonstrate that while both conjugates display similar cytotoxicity in vitro, their efficacy against tumors in vivo differs significantly.

Effect of Lysosomal Inhibitors on Cell Cycle Arrest Induced by huC242-Maytansinoid Conjugates.

Maytansinoids inhibit tubulin polymerization which leads to cell cycle arrest in the $G_2/M$ phase {Issell B. F., et al. Cancer Treat Rev, 5, 199-207 (1978)}, therefore both conjugates were checked for this activity. Samples of asynchronously growing cells were exposed to conjugate (3 nM), or DM1-SMe (10 nM see FIG. 16 for structure), or nocodazole (0.66 µM) another inhibitor of microtubule polymerization, at 37° C. for 20 h and the DNA content of the cells was then analyzed by flow cytometry. In cultures treated with nocodazole or DM1-SMe, greater than 50% of the cells were arrested in the $G_2/M$ phase (FIG. 7C, first row), compared to only 10% of untreated COLO 205 cells (typically about 60% in $G_1$ and 30% in S). In samples treated with either of the two conjugates, about 70-80% of the cells were arrested at the $G_2/M$ phase, indicating that the cell cycle effects of maytansinoid conjugates are similar to those of the free maytansinoids (FIG. 7C). No cell cycle arrest was induced by the conjugates in cells lacking the target antigen (data not shown).

To test whether uptake and processing of conjugates through lysosomes was necessary for their activity against cancer cells, $G_2/M$ arrest induced by conjugates in the presence of Bafilomycin A1, a lysosomal inhibitor, was examined. BafA1 selectively inhibits V-ATPase, a proton pump present in endosomes and lysosomes, which leads to neutralization of the pH in these vesicles {Drose, S., et al., J Exp Biol, 200, 1-8 (1997); Bowman, E. J., et al., Proc Natl Acad Sci USA, 85, 7972-76 (1988)}. The pH neutralization blocks trafficking from late endosomes to lysosomes and lysosomal processing, yet modestly affects the rate of internalization and recycling, and does not inhibit trafficking between endosomes and trans-Golgi {van Weert, A. W., et al., J Cell Biol, 130, 821-34 (1995); Oda, K., et al., Biochem Biophys Res Commun, 178, 369-77 (1991); Zetser, A., et al., J Cell Sci, 117, 2249-58 (2004)}. It was also found that the rate of internalization of a fluorescently modified huC242 was not affected by BafA1 (data not shown). The treatment of COLO 205 cells with BafA1 alone did not significantly alter the distribution of cells between the phases of the cell cycle (FIG. 7C). However in the presence of BafA1, $G_2/M$ arrest induced by either huC242-SMCC-DM1 or huC242-SPDB-DM4 was almost completely abolished (6-9% in $G_2/M$, FIG. 7C). In contrast, BafA1 treatment had a modest effect on the extent of $G_2/M$ arrest caused by the free maytansinoid, DM 1-SMe or by nocodazole (37%-39% in $G_2/M$, FIG. 7C). Similar results were also found when chloroquine, another lysosomal inhibitor that neutralizes pH by a different mechanism {Zetser A., et al., J Cell Sci., 117, 2249-58 (2004) and Homewood, C. A., et al., Nature, 235, 50-52 (1972)} was used. (FIG. 8). These findings were the first indication of the importance of lysosomal processing in the activation of both, huC242-SMCC-DM1 and huC242-SPDB-DM4.

Isolation of Maytansinoid Metabolites from huC242-Maytansinoid Conjugates.

To examine the fate of the maytansinoid drug upon incubation of target cells with an antibody-maytansinoid conjugate, we prepared conjugates with maytansinoids that were [$^3$H]-labeled at the C-20 methoxy group were prepared (see FIG. 16). Radiolabeled maytansinoid conjugates, huC242-SPDB-[$^3$H]DM4 (250 mCi/mmol) and huC242-SMCC-[$^3$H]DM1 (214 mCi/mmol), exhibit in vitro cytotoxicities similar to non-radiolabeled conjugate samples (data not shown). Cultures of $2 \times 10^6$ COLO 205 cells were exposed to $10^{-7}$ M [$^3$H]-labeled conjugates for periods of 5, 9, and 26 h, separated into cell and conditioned medium fractions, and each sample was extracted with acetone. Cells treated under these conditions remained viable with intact plasma membranes for at least the first 26 h of exposure as determined by Trypan blue staining (data not shown). The acetone extracts were analyzed for [$^3$H]-labeled metabolites by reverse phase HPLC. The chromatograms display signals for the amount of radioactivity in the acetone extracted samples from the thioether-linked huC242-SMCC-[$^3$H]DM1 treated cells (FIG. 9A). A control was prepared from an acetone extract of the conjugate used in the experiment in order to identify free maytansinoid species present in the huC242-SMCC-[$^3$H]DM1 sample prior to the exposure to cells (FIG. 9A; g). Two new, partially separated peaks of radioactivity with retention times of about 18.7 min and 19.2 min, respectively were identified in extracts from cells pellets. These metabolites are readily detectable after a 5-hour exposure, and increase by 9 and 26 h (FIG. 9A; a,c,e). These same metabolites were also detectable in the culture medium but not until the 9-h time point, and then were readily detectable in the 26-h sample. In separate experiments, the two metabolites were isolated and found by mass spectrometry to be the two isomers of lysine-$N^\epsilon$-SMCC-[$^3$H]DM1 (R or S configuration at the carbon of the thioether bond formed in the conjugation reaction; both peaks M+=1103.5; M+Na=1125.5).

The results from an analogous experiment with the disulfide-linked huC242-SPDB-[$^3$H]DM4 conjugate are also shown in FIG. 9B. Three distinct peaks of radioactivity with retention times of 20.5, 26.5, and 27 min were observed in the chromatograms derived from the cell pellets treated with huC242-SPDB-[$^3$H]DM4 for 5 and 9 h (FIG. 9B; a,c). Cells treated for 26 h yielded largely one peak with a retention time of 27 min (FIG. 9B; e), indicating that the metabolites eluting at 20.5 and 26.5 min had either been converted to the metabolite eluting at 27 min or were no longer present in the cells. The peak at 26.5 min has the same retention time as DM4. To further study this metabolite and to assess whether any of the other metabolites contained a free sulfhydryl group, an acetone extract from a 9-hour exposure was treated with N-ethyl-maleimide (NEM) and then subjected to HPLC (FIG. 2B; g). Following alkylation, the peak at 26.5 min, observed in the 5-h and 9-h samples, was replaced with a new peak at 25 min. This new peak co-elutes with a standard of the purified DM4-NEM reaction product (data not shown), suggesting that the metabolite at 26.5 min is indeed DM4.

The corresponding chromatograms associated with the conditioned media from treated cells are displayed in FIG. 9B (b, d and f). After 5 h of exposure, no metabolites can be detected—the peaks present are also visible in the control chromatogram of the acetone extract of the conjugate sample (FIG. 9B; h). After 9 h of exposure, however, the unknown metabolite with a retention time of 20.5 min that was observed in cells after 5 h can be detected in the medium, and after 26 h, two additional metabolites with retention times of 18.5 min and 27 min were present. The unique metabolite in the medium which elutes at 18.5 min was found to have the same retention time as the mixed disulfide between DM4 and cysteine (S-cysteinyl-DM4, data not shown). RPMI 1640 medium contains 0.21 mM cystine, and separate experiments have shown that DM4 under these conditions reacts rapidly ($t_{1/2}$<1 hour) to form S-cysteinyl-DM4 through a thiol-disulfide interchange reaction (data not shown). Thus, the S-cysteinyl-DM4 disulfide compound would be expected to form in the medium if the DM4 observed in the cell pellet leaves the cells. To further test whether any of the metabolites in the media was a disulfide compound, a cell supernatant sample from a 26-hour exposure was divided into two equal portions of which one was subjected directly to chromatography, and the other portion was treated with DTT and selenol before chromatography to reduce all disulfide bonds (18). Following reduction, all of the peaks of radioactivity in the chromatograms disappeared except the peak eluting at 27 min and a single new peak appeared with a retention time of 26.5 min, which is that of DM4 (FIG. 10). Thus, the metabolites eluting at 18.5 min and 20.5 min, but not the metabolite at 27 min, are DM4 species containing a disulfide-linked substituent. In separate experiments, the unknown metabolites eluting at 20.5 and 27 min were found to have a mass consistent with lysine-$N^\epsilon$-SPDB-DM4 (M+Na=1048.4) and S-methyl-DM4 (M+Na=816.4/M+K=832.5), respectively In the above experiments, $2\times10^6$ COLO 205 cells were incubated in 3 mL of medium containing $10^{-7}$ M conjugate. From this large amount of conjugate, less than 20% of the conjugate-bound maytansinoid was recovered in the identified maytansinoid metabolites after incubation with the cells for 26 hours (dotted line in FIG. 11A; c represents 20% level). In a separate experiment following the fate of huC242-SPDB-[$^3$H]DM4 that was bound to cells at 4° C., it was determined that within a 22 h period at 37° C., 73% of the conjugated DM4 bound to COLO 205 cells was converted into the four maytansinoid metabolites, DM4, S-cysteinyl-DM4, lysine-$N^\epsilon$-SPDB-DM4, and S-methyl-DM4 (FIG. 12). These metabolites are believed to represent the majority of (if not all) the metabolites formed in the cellular activation process. Moreover, production of these maytansinoid metabolites was not observed when COLO 205 cells were incubated with disulfide-linked or SMCC-linked maytansinoid conjugates which do not bind target antigens on these cells (FIG. 13).

The Kinetics for the Accumulation of Metabolites and Cell Cycle Arrest

The peak areas of radioactivity associated with the metabolites generated from huC242-SMCC-[$^3$H]DM1 and from huC242-SPDB-[$^3$H]DM4 (FIG. 9) were determined and converted to pmol of maytansinoid as described in Materials and Methods. The results are shown in FIG. 11A as accumulation of the maytansinoid metabolites over time from the addition of the conjugates to the cells (T=0). Panel (a) shows the accumulation of lysine-$N^\epsilon$-SMCC-DM1, the single metabolite from huC242-SMCC-[$^3$H]DM1, in the cell pellet and in the medium. The concentration of the metabolite in the cells reaches a steady state after 9 h of incubation, which may be due to the saturation of an intracellular binding site. This maytansinoid metabolite begins to appear in the medium at 9 h, suggesting efficient efflux of the charged lysine-$N^\epsilon$-SMCC-DM1 species across the plasma membrane. FIG. 11A (b) shows the accumulation of the three stable metabolites generated from huC242-SPDB-[$^3$H]DM4, in the cell pellet and in the medium. The intracellular amount of the disulfide compound, lysine-$N^\epsilon$-SPDB-DM4, declines over the observed period of 26 h, presumably through disulfide cleavage to DM4 in the intracellular reducing environment, followed by subsequent conversion of the resulting free thiol, DM4, to the stable S-methyl-DM4 derivative. Very little if any DM4 was observed inside the cells after 9 h of incubation, indicating rapid methylation probably catalyzed by a methyl transferase. The total intracellular accumulation of metabolites reaches a steady state after 9 h of exposure to either conjugate and the levels of metabolites at the steady state are about the same for both conjugates (FIG. 11A) suggesting that the conjugates share the same rate-limiting step with respect to production of the metabolites and that these metabolites likely bind to the same intracellular target.

Since only about 9 h is required for intracellular accumulation of metabolites to reach the steady state level, an experiment was conducted to determine whether $G_2/M$ arrest induced by either conjugate can occur within that timeframe. COLO 205 cells were first synchronized with a 24-hr treatment of aphidicolin, a reversible DNA replication inhibitor that blocks cells in S phase (Ikegami S. et al., Nature, 275, 458-460 ((1978)). Since the majority of the asynchronous population of COLO 205 cells were in $G_1$ phase, most of the aphidicolin-treated cells arrested in the beginning of S phase, which cannot be distinguished from $G_1$ phase in the FACS analysis (FIG. 11B, top picture). The synchronized cells were then released from the arrest by the removal of aphidicolin, and either left untreated, or treated with DM1-SMe or with either conjugate. Untreated cells immediately continue with DNA synthesis, and the majority is in $G_2/M$ phase (59%) after 5 h (FIG. 11B), and has undergone mitosis at 10 h and are in $G_1$ phase (76%). In contrast, the majority of cells treated with DM1-SMe or either conjugate are in $G_2/M$ phase (75% to 85%) after 10 h and after 18 h, indicating that sufficient amounts of active drug species have accumulated intracellularly to induce mitotic arrest when the aphidicolin-released cells reached mitosis. Therefore, COLO 205 cells require as little as 5 h, but no more than 10 h to produce enough of active drug metabolites to cause cell cycle arrest. Thus, the kinetics of $G_2/M$ phase arrest induced by these conjugates correlate with the time required to reach the steady state level of intracellular accumulation of the drug metabolites.

Activity of Maytansinoid Metabolites

The two major metabolites, S-methyl-DM4 and lysine-$N^\epsilon$-SMCC-DM1, were synthesized and tested for their in vitro cytotoxicity against COLO 205 cells and Namalwa cells. S-methyl-DM4 was highly cytotoxic with an $IC_{50}$ value of 2 pM against both cell lines, while lysine-$N^\epsilon$-SMCC-DM1 was about $10^5$-fold less potent against both cell lines with an $IC_{50}$ value of 0.1 µM (data not shown). This difference may be explained by the different charge status of the compounds. The charged lysine derivatives are expected to penetrate cell membranes very inefficiently such that high external concentrations are needed to reach the required toxic intracellular concentrations, whereas penetration of cell membranes is efficient for the neutral lipophilic S-methyl-DM4 compound.

Accumulation of the lysine-$N^\epsilon$-SMCC-DM1 metabolite from the non-cleavable conjugate is coincident with the observed formation of the potent S-methyl-DM4, DM4, and lysine-$N^\epsilon$-SPDB-DM4 from the cleavable conjugate. This suggests that the lysine-$N^\epsilon$-SMCC-DM1 metabolite is as potent as the metabolites from the cleavable conjugate when delivered intracellularly and that all of the maytansinoid metabolites are active when produced in the cell. The cell cycle arrest of both the cleavable and non-cleavable conjugates was abrogated in the presence of the lysosomal inhibitor BafA1 (FIG. 7C). If the lysine-$N^\epsilon$-SMCC-DM1 metabolite and the other metabolites observed from the cleavable conjugate arrest cells, BafA1 should prevent their formation. To investigate this possibility, COLO 205 cells were incubated at 37° C. for 22 h with $10^{-7}$ M huC242-SMCC-[$^3$H]DM1 or huC242-SPDB-[$^3$H]DM4 conjugate in the presence or in the absence of 300 nM BafA1. BafA1 abolished the formation of both the lysine-$N^\epsilon$-SMCC-DM1 from the thioether linked conjugate, and the S-methyl-DM4 from the disulfide linked conjugate (FIG. 14A). In addition, no metabolites were detected in the medium of cells treated with either conjugate in the presence of BafA1 (data not shown). These results suggest that the lysine metabolites are toxic when delivered intracellularly and that lysosomal processing is necessary for the production of all the observed metabolites.

The rate of release of total maytansinoids is approximately constant for 20 h, yet few metabolites are observed in the medium until after 9 h by which time the maximum amount of metabolites in the cell has been achieved (FIG. 11A, c). This suggests that the binding of metabolites to the intracellular target affects the rate of the efflux, and that less toxic derivatives of DM4 may efflux at earlier times if the decreased toxicity is due to a lower binding affinity to the intracellular target. To investigate this possibility, the cellular processing of a conjugate prepared from a 50-fold less potent (data not shown) isomer of DM4, D-[$^3$H]DM4, was studied. DM4 has the natural L-N-methyl-alanyl group in the side chain, while D-DM4 has its D-N-methyl-alanyl isomer. HuC242 conjugates prepared with the D-isomer of DM4 were at least 700-fold less toxic to COLO 205 cells than the corresponding L-isomer conjugate (data not shown). Samples of $2\times10^6$ COLO 205 cells were exposed to $10^{-7}$ M huC242-SPDB-D-[$^3$H]DM4 conjugate and $10^{-7}$ M huC242-SPDB-[$^3$H]DM4 as a control at 37° C. for various periods of time and analyzed by reverse phase HPLC (FIG. 15). Almost no metabolites are observed in the cells treated with huC242-SPDB-D-[$^3$H]DM4 even after 30 h, while an unknown metabolite with a retention time of 22 min was observed in the media after only 5 h of incubation and steadily increases after 9, 22, and 30 h of exposure. The identity of the unknown was confirmed as lysine-$N^\epsilon$-SPDB-D-DM4 by MS analysis (M+Na=1048.5).

The amount of the lysine-$N^\epsilon$-SPDB-D-DM4 metabolite after 30 h was similar to the sum of all the metabolites from the control cells treated with huC242-SPDB-[$^3$H]DM4 after 30 h (FIG. 14B), suggesting that the two conjugates with the D and L isomers of DM4 are both internalized and processed to their respective lysine-DM4 adducts at similar rates. The explanation for the lack of an appreciable accumulation of D-DM4, S-cysteinyl-D-DM4 and S-methyl-D-DM4 from the conjugate with the D isomer of DM4 may be explained by poor intracellular binding and rapid efflux of lysine-$N^\epsilon$-SPDB-D-DM4.

Example 3

Synthesis of Some Thiomethyl Maytansinoids (FIG. 17)

$N^{2'}$-deacetyl-$N^{2'}$-(3-methylthio-1-oxopropyl)-maytansine (S-Methyl-DM1, DM1Me): To a solution of $N^{2'}$-deacetyl-N-$^{2'}$(3-mercapto-1-oxopropyl)-maytansine (DM1, 30 mg, 0.041 mmol) in dimethylacetamide (0.25 mL) was added a solution of iodomethane (5.8 mg, 0.041 mmol) in 0.2 mL of dimethylacetamide under an argon atmosphere, with magnetic stirring. Diisopropylethylamine (5.0 mg, 0.041 mmol) was then added and the reaction was stirred for 3 hours. Purification by high pressure liquid chromatography using a reverse phase C18 column and a gradient of deionized water and acetonitrile gave 20 mg (65% yield) of the desired product DM1 Me. Mass spectrum: found 774.5 (M+Na$^+$). calculated 774.3 (M+Na$^+$). $^1$H NMR (CDCl$_3$) δ 0.84 (3H, s), 1.33 (3H, d, J=5 Hz), 1.35 (3H, d, J=5 Hz), 1.60 (3H, s), 1.68 (3H, s), 2.05 (3H, s) 2.22 (1H, dd, J=3 Hz, 14 Hz, 2.60-2.82 (2H, m), 2.88 (3H, s), 3.08-3.20 (2H, m), 3.25 (3H, s), 3.39 (3H, s), 3.55 (1H, d, J=9 Hz), 3.71 (1H, d, J=12 Hz), 4.02 (3H, s), 4.32 (1H, t, J=10 Hz), 4.81 (1H, dd, J=3 Hz, 12 Hz), 5.45 (1H, q, J=7 Hz), 5.67 (1H, dd J=9 Hz, 15 Hz), 6.25 (1H, s), 6.47 (1H, dd, J=11 Hz, 15 Hz), 6.70 (1H, d, J=1.5 Hz), 6.75 (1H, d, J=11 Hz), 6.86 (1H, d, J=1.5 Hz).

$N^{2'}$-deacetyl-$N^{2'}$-(4-methylthio-4-methyl-1-oxopentyl)-maytansine (S-Methyl-DM4, DM4Me): To a solution of $N^{2'}$-deacetyl-$N^{2'}$-(4-mercapto-4-methyl-1-oxopentyl)-maytansine (DM4, 12 mg, 0.015 mmol) in dimethylacetamide (0.1 mL) was added a solution of iodomethane (2.2 mg, 0.015 mmol) in dimethylacetamide (0.04 mL) under an argon atmosphere, with magnetic stirring. Diisopropylethyl amine (2.0 mg, 0.015 mmol) was then added and the reaction was stirred for 3 hours. The desired product was isolated by reverse phase high pressure liquid chromatography using a C18 column and a gradient of deionized water and acetonitrile (7 mg, 57% yield). Mass spectrum. Found 816.4 (M+Na$^+$) Calculated 816.3 (M+Na$^+$); $^1$H NMR (CDCl$_3$) δ 0.798 (3H, s), 1.219 (3H, d, J=15.6 Hz), 1.294 (6H, d, J=6.4 Hz), 1.331 (3H, d, J=15.6 Hz), 1.470 (2H, m), 1.639 (3H, s), 1.76 (3H, s), 1.805-1.966 (2H, m), 1.826 (1H, dd, J=19.2, 7.2 Hz), 2.179 (1H, dd, J=17.6, 11.2 Hz), 2.595 (2H, m), 2.877 (3H, s), 3.035 (1H, d, J=10 Hz), 3.113 (1H, d, J=12.4 Hz), 3.234 (3H, s), 3.353 (3H, s), 3.500 (1H, d, J=8.8 Hz), 3.634 (1H, d, J=12.8 Hz), 3.819 (1H, d, J=1.6 Hz), 3.983 (3H, s), 4.273 (1H, t), 4.787 (1H, dd, J=15.2, 8.8 Hz), 5.414 (1H, q, J=6.8 Hz), 5.682 (1H, dd, J=24.4, 6 Hz), 6.214 (1H, s), 6.424 (1H, dd, J=26.4 and 4 Hz), 6.649 (1H, d, J=1.6 Hz), 6.731 (1H, d, J=11.2 Hz).

What is claimed is:

1. An isolated alkylated maytansinoid, which has the following formula:

wherein, n=1, and May=maytansinoid.

2. The isolated alkylated maytansinoid of claim 1, wherein, MayO(C═O)CH(Me)N(CH$_3$)COCH$_2$CH$_2$(CMe$_2$)$_n$S represents a $N^{2'}$-deacetyl-N-$^{2'}$(4-methyl-4-mercapto-1-oxopentyl)-maytansine (DM4) residue.

3. Isolated lysine-$N^\epsilon$-SPDB-DM4.
4. Isolated S-cysteinyl-DM4.
5. Isolated S-methyl-DM4.

* * * * *